US009855186B2

(12) United States Patent
Goldenberg et al.

(10) Patent No.: US 9,855,186 B2
(45) Date of Patent: Jan. 2, 2018

(54) DEVICES AND METHODS FOR PROMOTING FEMALE SEXUAL WELLNESS AND SATISFACTION

(71) Applicant: AYTU Women's Health, LLC, Englewood, CO (US)

(72) Inventors: Alex Goldenberg, San Francisco, CA (US); Eric A Goldfarb, Belmont, CA (US); Jose L Cordoba, Malaga (ES)

(73) Assignee: AYTU WOMEN'S HEALTH, LLC, Englewood, CO (US)

(*) Notice: Subject to any disclaimer, the term of this patent is extended or adjusted under 35 U.S.C. 154(b) by 402 days.

(21) Appl. No.: 14/467,018

(22) Filed: Aug. 24, 2014

(65) Prior Publication Data

US 2015/0328081 A1 Nov. 19, 2015

Related U.S. Application Data

(60) Provisional application No. 61/993,041, filed on May 14, 2014.

(51) Int. Cl.

*A61F 5/00* (2006.01)
*A61H 19/00* (2006.01)

(Continued)

(52) U.S. Cl.

CPC .......... *A61H 19/34* (2013.01); *A61H 9/0057* (2013.01); *A61H 19/32* (2013.01); *A61H 23/02* (2013.01);

(Continued)

(58) Field of Classification Search

CPC ........ A61H 19/00; A61H 19/30; A61H 19/34; A61H 9/0057

(Continued)

(56) References Cited

U.S. PATENT DOCUMENTS

| | | | |
|---|---|---|---|
| 4,608,000 | A | 8/1986 | Tominaga |
| 4,786,240 | A | 11/1988 | Koroly et al. |

(Continued)

FOREIGN PATENT DOCUMENTS

| | | |
|---|---|---|
| WO | 2015031216 | 3/2015 |

OTHER PUBLICATIONS

Santra et al, Fabrication and testing of a magnetically actuated micropump, Sensors and Actuators B 87 (2002) 358-364.

(Continued)

*Primary Examiner* — John Lacyk

(74) *Attorney, Agent, or Firm* — Sheridan Ross PC

(57) ABSTRACT

Devices, systems, and methods for promoting female sexual wellness and function. The devices, systems, and methods encourage clitoral engorgement using suction over the clitoris combined with vibratory stimulation. In some embodiments, a device is capable of operation in an automatic attachment (autoattach) mode, in which detecting attachment of the device to user tissue (e.g. through detection of a positive pressure in a tissue-contacting chamber) automatically triggers starting a suction pump to secure the device in place. Suction settings such as a target negative pressure may be determined according to a dynamically-evaluated quality of a seal established between the device and user tissue. The quality of the seal may be determined by identifying drops in the absolute value of negative pressure that are not readily compensated for by the suction pump.

15 Claims, 17 Drawing Sheets

(51) Int. Cl.
*A61H 9/00* (2006.01)
*A61H 23/02* (2006.01)

(52) U.S. Cl.
CPC ................ *A61H 2201/0176* (2013.01); *A61H 2201/0207* (2013.01); *A61H 2201/10* (2013.01); *A61H 2201/1207* (2013.01); *A61H 2201/1238* (2013.01); *A61H 2201/165* (2013.01); *A61H 2201/5007* (2013.01); *A61H 2201/5012* (2013.01); *A61H 2201/5035* (2013.01); *A61H 2201/5043* (2013.01); *A61H 2201/5046* (2013.01); *A61H 2201/5048* (2013.01); *A61H 2201/5058* (2013.01); *A61H 2201/5071* (2013.01); *A61H 2201/5082* (2013.01); *A61H 2201/5084* (2013.01); *A61H 2201/5087* (2013.01); *A61H 2201/5097* (2013.01)

(58) Field of Classification Search
USPC ...................................................... 600/38–41
See application file for complete search history.

(56) References Cited

U.S. PATENT DOCUMENTS

| | | | |
|---|---|---|---|
| 4,828,464 | A | 5/1989 | Maier et al. |
| 4,859,152 | A | 8/1989 | Kimura et al. |
| 5,011,379 | A | 4/1991 | Hashimoto |
| 5,529,465 | A | 6/1996 | Zengerle et al. |
| 5,599,174 | A | 2/1997 | Cook et al. |
| 6,179,586 | B1 | 1/2001 | Herb et al. |
| 6,203,288 | B1 | 3/2001 | Kottke |
| 6,203,291 | B1 | 3/2001 | Stemme et al. |
| 6,514,047 | B2 | 2/2003 | Burr et al. |
| 6,589,028 | B1 | 7/2003 | Eckerbom et al. |
| 6,771,791 | B2 | 8/2004 | Shelley et al. |
| 7,033,148 | B2 | 4/2006 | Bunner et al. |
| 7,104,767 | B2 | 9/2006 | Lee |
| 7,167,573 | B2 | 1/2007 | Williamson |
| 7,885,418 | B1 | 2/2011 | Hallman |
| 8,147,221 | B2 | 4/2012 | Fu et al. |
| 8,272,850 | B2 | 9/2012 | Stenberg |
| 8,366,414 | B2 | 2/2013 | Kaufmann et al. |
| 8,579,837 | B1 | 11/2013 | Makower et al. |
| 2005/0254971 | A1 | 11/2005 | Ohya et al. |
| 2007/0237352 | A1 | 10/2007 | Andersen et al. |
| 2010/0165784 | A1 | 7/2010 | Jovanovich et al. |
| 2010/0221131 | A1 | 9/2010 | Noritsugu et al. |
| 2011/0237863 | A1 | 9/2011 | Ricci et al. |
| 2011/0274566 | A1 | 11/2011 | Amirouche et al. |
| 2012/0315157 | A1 | 12/2012 | Rochat |
| 2013/0230419 | A1 | 9/2013 | Lucas |
| 2014/0003978 | A1 | 1/2014 | Ishii et al. |

OTHER PUBLICATIONS

Zhi et al, Design of a Micro Pump Actuator Using a Thin Film Permanent Magnet, 16th International Conference on Mechatronics Technology, Oct. 16-19, 2012, Tianjin, China.

DEVICES AND METHODS FOR PROMOTING FEMALE SEXUAL WELLNESS AND SATISFACTION

CROSS-REFERENCE TO RELATED APPLICATIONS

This application claims the benefit of and priority to U.S. provisional application 61/993,041, filed May 14, 2014, titled "Miniature Pumps, Actuators And Related Devices And Methods For Making And Use" which is hereby incorporated herein, in its entirety, by reference.

FIELD OF THE INVENTION

Embodiments of the present invention relate generally to devices and methods and more particularly to promoting female sexual wellness and satisfaction. In particular, certain embodiments are useful for promoting, facilitating, stimulating, or enhancing sexual desire, arousal or satisfaction in a female.

BACKGROUND OF THE INVENTION

Clitoral vascular engorgement plays an important role in female sexual desire, arousal and satisfaction. Sexual arousal results in smooth muscle relaxation and arterial vasodilation within the clitoris. The resultant increase in blood flow leads to tumescence of the glans clitoris and increased sexual arousal.

The female sexual response cycle affects the incidence of a satisfying sexual experience (SSE) for women. The cycle includes the states of (i) emotional and physical satisfaction, leading to (ii) emotional intimacy, leading to (iii) being receptive to sexual stimuli, leading to (iv) sexual arousal, leading to (v) arousal and sexual desire, which takes the cycle back around to the state of (i) emotional and physical satisfaction. Spontaneous sex drive can occur between states (ii) and (iii), between states (iii) and (iv), and/or between states (iv) and (v).

Female sexual wellness and satisfaction can be addressed by embodiments of the present invention.

BRIEF SUMMARY OF THE INVENTION

Certain embodiments of the present invention are related to systems, methods and computer-readable media for promoting female sexual arousal; for managing an attachment of a suction device to a user's tissue, in particular using an auto-attachment operating mode; and for managing an operation of a suction pump of such a device according to indicators of leaks and/or quality of the seal established between the device and user tissue.

DETAILED DESCRIPTION OF THE INVENTION

Figure 1A:
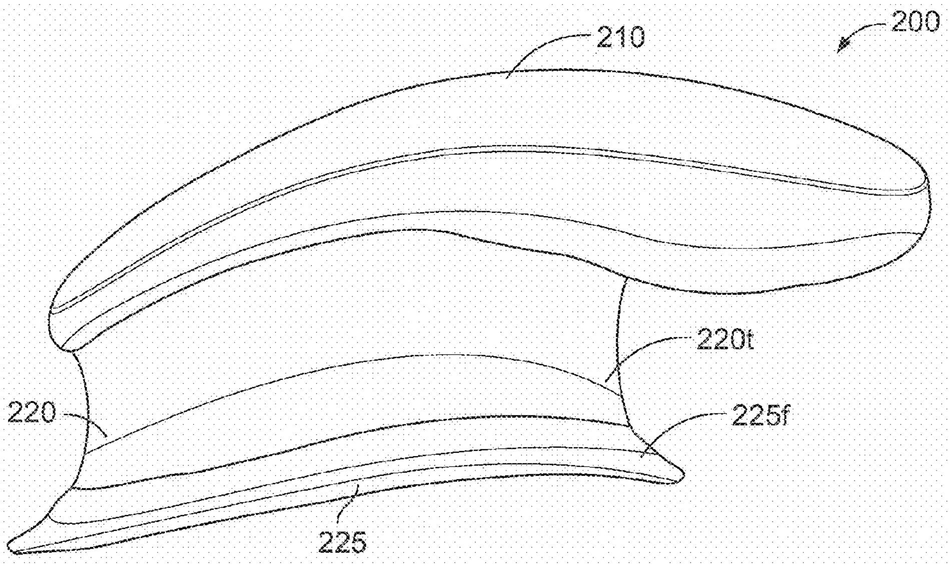
FIGS. 1A through 1D illustrate various views of a device according to an embodiment of the invention.
Figure 1B:
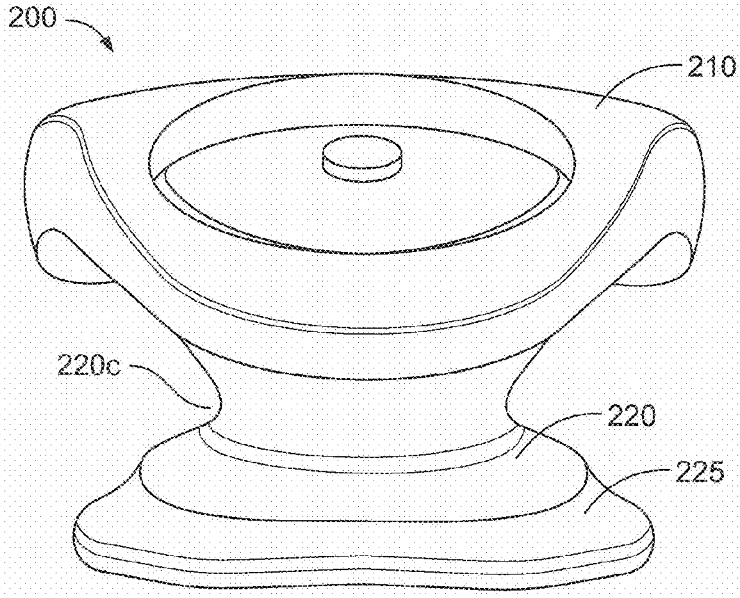
Figure 1C:
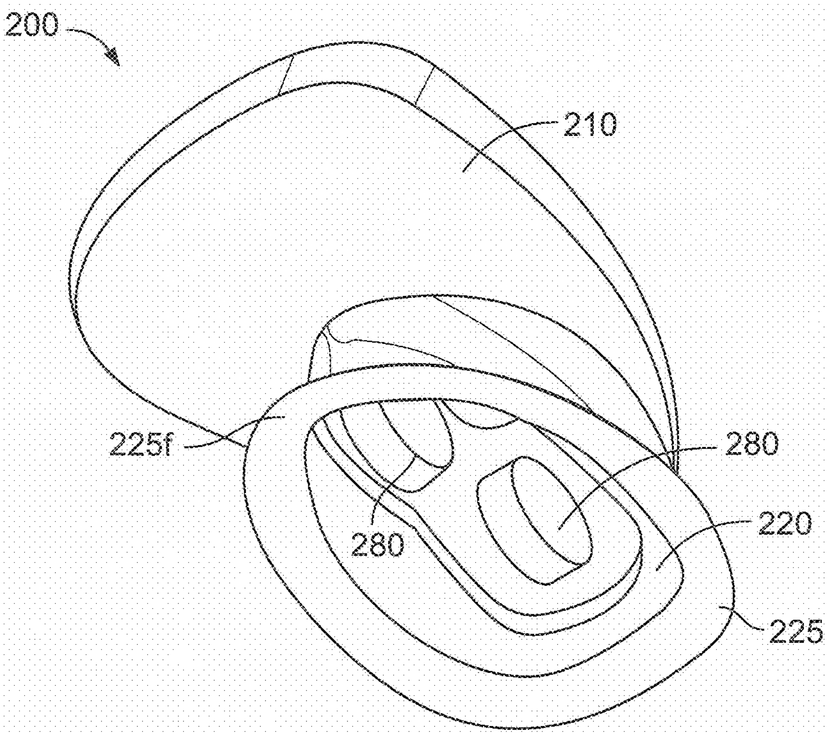
Figure 1D:
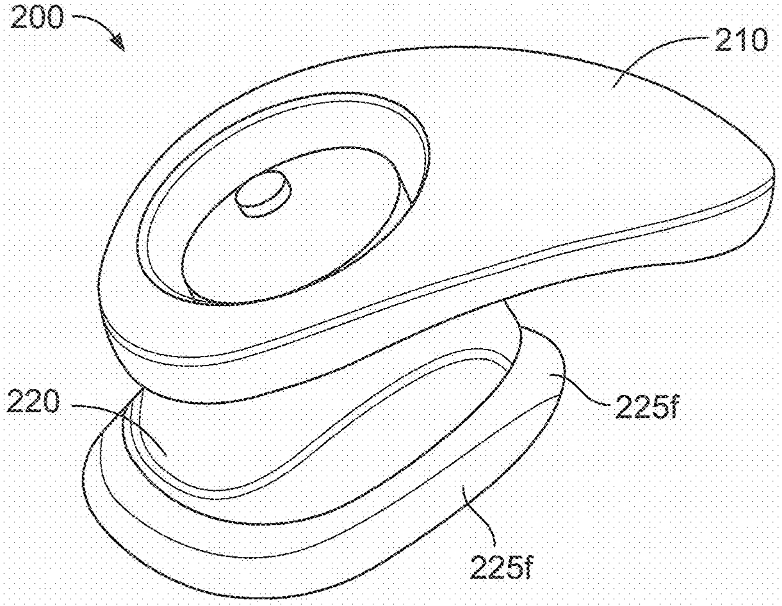

Embodiments of the present invention described herein, including the figures and examples, are useful for promoting female sexual wellness and function.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Short summaries of certain terms are presented in the description of the invention. Each term is further explained and exemplified throughout the description, figures, and examples. Any interpretation of the terms in this description should take into account the full description, figures, and examples presented herein.

The singular terms "a," "an," and "the" include plural referents unless the context clearly dictates otherwise. Thus, for example, reference to an object can include multiple objects unless the context clearly dictates otherwise. Similarly, references to multiple objects can include a single object unless the context clearly dictates otherwise.

The terms "substantially," "substantial," and the like refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

The term "about" refers to a value, amount, or degree that is approximate or near the reference value. The extent of variation from the reference value encompassed by the term "about" is that which is typical for the tolerance levels or measurement conditions.

The term "stimulator" refers to elements that provide stimulation using mechanical motion (such as vibration), electrical stimulation, temperature, or other sensory stimulation.

All recited connections may be direct connections and/or indirect operative connections through intermediary structure.

A set of elements includes one or more elements.

Unless otherwise stated, performing a comparison between two elements encompasses performing a direct comparison to determine whether one element is larger (or larger than equal to) the other, as well as an indirect comparison, for example by comparing a ratio or a difference of the two elements to a threshold.

Unless otherwise required, any described method steps need not be necessarily performed in a particular illustrated order. A first element (e.g. data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself. Computer readable media encompass storage (non-transitory) media such as magnetic, optic, and semiconductor media (e.g. hard drives, optical disks, flash memory, DRAM), as well as communications links such as conductive cables and fiber optic links. According to some embodiments, the present invention provides, inter alia, computer systems and/or mobile communication devices programmed to perform the methods described herein, as well as computer-readable media encoding instructions to perform the methods described herein.

We have discovered that engorgement and vibration together are a powerful combination such that engorgement creates a more suitable mechanical back-board for the pacinian corpuscles to be stimulated and that applying both simultaneously should produce more profound effects than either applied alone. In both sexes, engorgement of the sexual organs is the key physiological target in that engorgement is fundamental to achieve an SSE. Embodiments described herein provide methods and devices for engorging sexual organs to better propagate vibrational energy.

Certain prior art stimulation devices, such as vibrators, provide relatively diffuse stimuli. That is, the vibrating motion supplied by a vibrator is applied relatively evenly over the clitoris and surrounding tissue. In certain vibrating devices that are capable of delivering vibration over a more tightly focused area, the frequency and magnitude of the vibration may still present a relatively diffuse vibratory motion to clitoral tissue. Additionally, much of the vibration of prior art vibrators is lost in vibrating the handle, housing and the user's hand or other portion of their body.

Advantageously, certain embodiments described herein are capable of providing complex patterns of suction. Such complex suction waveforms can provide a comparatively organic stimulation experience as compared to prior art mechanical stimulation devices. For some users, the variable suction patterns, algorithms waveforms of certain embodiments can provide engorgement and stimulation such that effective arousal is achieved without the use of vibration.

Certain embodiments of devices disclosed herein use suction to draw tissue into contact with vibrating elements. Certain devices remain in contact with tissue by virtue of the suction applied to the tissue. Yet another benefit of isolating vibration in devices is that the airtight seal between the device and tissue is not substantially disrupted by the vibration. This type of vibration isolation involves substantially isolating the sealing elements of the device from the vibrating elements in the device.

The compact size of devices disclosed herein makes them capable of being discreetly worn and capable of being carried in a purse. Yet, devices disclosed herein are sized and configured to be accessible and controllable while being worn. Devices disclosed herein may be usable prior to and during intercourse or as a program for recruitment of blood flow and nerve sensitization of tissue. Devices disclosed herein may be adjustable and customizable and provide selectable, variable suction and vibrational properties. Devices disclosed herein may be capable of being controlled remotely, such as by a smartphone. Devices discloses herein may be capable of promoting and/or sustaining female sexual arousal.

Advantageously, devices disclosed herein use relatively low power motors to produce focused, spatially-differentiated vibration.

In certain embodiments, proper placement can be achieved by activating one or more motors to a detectable level of vibration to allow the user to center the stimulatory effect about the clitoris. By pre-activating the motors during placement, the user can customize the fit and determine the most effective location for vibrational simulation and/or suction stimulation.

Specific aspects of the device features may include some or all of the following: (i) the user is able to set suction to the level that is comfortable to them; (ii) the user is able to detach the suction tube from the device without losing vacuum pressure that leads to device detachment; (iii) the user is able to control vibration function by means of wireless remote control; (iv) the user interface is via iOS, Android, or other mobile operating system application on a Bluetooth enabled device or via an RF or Bluetooth key fob styled controller; (v) the user is able to control vibration parameters such as pattern transition speed and vibration amplitude; (vi) power is provided via an internal rechargeable battery, not accessible to the user; (vii) the user is able to control/direct vibration focus through pointing with finger on a wireless enabled device; (viii) the user is able to control degree of motor overlap; (ix) the motor overlap optimized for organic feel; (x) the device is enabled with basic rotational motor patterns; (xi) the device withstands an external force applied to the external shell (over the attachment area) by the user; (xii) the shell withstands sufficient vacuum cycles without loss of integrity; (xiii) the user is able to customize the motor pattern including direction, motor selection, looping, and save/recall the customized pattern; and (xiv) the user is able to customize the suction pattern and save/recall the customized pattern. Studies have shown that different areas of the female brain are activated when the clitoris is self-stimulated than when the clitoris is stimulated by a partner and that often times a female can achieve orgasm easier through self-stimulation than when stimulated by a partner. With the certain embodiments of the devices described herein, the female can record the stimulation pattern that allows her to achieve orgasm through self-stimulation and store it in the devices memory. Subsequently, the device can be used during intercourse to play the saved pattern such that the female can achieve orgasm as if she were self-stimulating.

Preferred attributes of certain embodiments include: (i) user adjustable suction for fixation and blood flow recruitment; (ii) user adjustable vibration for blood flow recruitment and nerve stimulation; (iii) spatially differentiated stimulation via macro-motion or isolation & control of multiple stimulation sources; (iv) tether-less and wearable during intercourse; and (v) customizable & reusable.

Certain embodiments of the device include onboard circuitry, power, pump, or other electronic features. For example, the device includes an antenna for interacting with the remote controller, such as an RF antenna. The device includes a battery.

Certain embodiments of the device are controlled by a remote drive connected via drive cable to vibratory and/or suction elements inside the wearable part of the device.

Certain embodiments of the device provide variable suction. In such embodiments, the user may rapidly and easily adjust the suction levels. Further, in certain embodiments the variable suction is programmable such that the amount of suction applied by the device can vary according to a pattern. In some instances, the suction pattern is complementary to the vibration and/or macroscopic motion patterns. The device controller includes a means for controlling the suction patterns, pre-loaded suctions patterns, user-configurable suctions patterns, or combinations thereof. The device controller enables the user to selected pre-loaded combinations of a suction pattern, a vibrational pattern, and/or a macroscopic motion pattern and also enables the user to design and select customized combinations.

The control systems, software, firmware, algorithms, and system architecture disclosed herein can be used in connection with devices disclosed in U.S. provisional application 61/981,836, filed Apr. 20, 2014, titled "Devices and Methods for Promoting Female Sexual Wellness" which is hereby incorporated herein, in its entirety, by reference.

FIGS. 1A, 1B, 1C, and 1D illustrate different views of device 200 according to another embodiment. Device 200 includes device body 210, which can house controller circuitry, and suction chamber 220. The controller circuitry can be accessed using an interface mounted on device body 210 and/or via a remote controller. The remote controller can be physically tethered to device body 210 or it can be wirelessly connected. Suction body 220 includes sealing and flange 225, which is adapted to provide a substantially airtight seal against tissue. The various views of FIGS. 1A, 1B, 1C, and 1D illustrate certain features of the shape and form of device 200 which promote comfortable, discreet, and secure attachment of device 200. For example, device 200 is sized such that the attachment area, defined by area where sealing flange 225 meets suction chamber 220, fits between the labia majora inferior to the clitoris and device body 210 may exit the labia majora superior to the clitoris. Further, the taper of the upper section of suction chamber 220 facilitates comfortable, discreet, and secure fit. The curve of device body 210 can help device 200 conform to the user and allow discreet placement inside garments.

Specifically, the front section **225*f* of sealing flange 225 is placed superior to the clitoris and tucked under the anterior commissure of the labia majora. In that position, the labia majora inferior to the anterior commissure can snugly engage the tapered section 220*t* of suction chamber 220 such that substantially the entire front and lateral portions of the sealing flange 225 are tucked under the labia majora. Advantageously, the tapered section 220*t* of suction chamber 220 allows the labia majora to comfortably engage a comparatively narrower section of the device while vaginal tissue superior to the vaginal orifice engages the comparatively wider sealing flange 225**.

Proper placement of device 200 can be easily and repeatably achieved by following a few steps. For example, when a user first attempts to place the device, they may benefit from the use of a mirror such that the user's head and shoulders are propped up and they can use the mirror to observe themselves placing the device. The user can open their outer labia so that they can see their inner labia and the hooded glans of the clitoris. Users can identify a groove within their outer labia that runs along the inner labia at the bottom and the hooded clitoris at the top. Device 200 can be effective when the sealing flange 225 is centered over the clitoris and the comparatively soft edges of the sealing flange 225 fit into the groove. In some cases the user can tug their outer labia to make space for the outer ring to fit snugly in the groove. The vibratory motors can then fit snugly around the glans of the clitoris. In some instances, the user can apply an amount of a lubricant (such as a water-based lubricant) to coat their inner and outer labia, the glans of the clitoris, the hood of the clitoris, and the comparatively soft edges of the sealing flange 225. The user can activate the vibratory motors at a relatively low power setting to help place the device. By using the sensation from the low power vibrations as a guide, the user can ensure that the clitoris is placed snugly within the space defined by the inner portions of the vibratory motors. In some cases, the user can apply stimulation with their inner labia separated. A properly placed device will be high enough on the user's vulva to effectively cup the clitoris and not block the urethra or the vaginal opening.

In certain embodiments, multiple vibratory-disc, or miniature coin-style, motors are embedded in the wall of a flexible suction chamber. In certain embodiments, the motors are embedded in a flexible membrane, which is attached to the walls of the suction chamber. When suction is applied, tissue is brought into contact with the stimulator. The motors can be controlled by controller circuitry to produce one or more of the following patterns: (i) all on; (ii) clockwise; (iii) counter clockwise; (iv) up-down; (v) lateral; (vi) all pulse; (vii) selected motor pulse; (viii) gradients in frequency; and (ix) gradients in amplitude. The translation of the vibratory pattern and spatial isolation of the motors may produce a desired effect of simulating macroscopic motion without incorporation parts that actually move in macroscopic dimensions. Stiffening members may be added to the motor mounts to vary and/or isolate vibration. The inner surface of the membrane may be textured to transmit vibration to tissue. The flexible membrane reduces or eliminates the coupling of the motor vibration to the device housing and increases or maximizes energy delivery into the tissue.

In one embodiment, patterns are created by multiple vibratory motors. After a motor is activated it can be completely deactivated or have its power reduced such that a pattern of higher power vibration rotates around the array of motors. Rotational patterns, lateral patterns, vertical patterns, and combination thereof can be created by selectively activating and deactivating motors. All such patterns are within the scope of the invention disclosed herein regardless of the number of motors. Further, in embodiments herein in which vibratory motors are depicted as providing the stimulation, other stimulators can be used in place of or in addition to the vibratory motors. That is, one or more of the vibratory motors can instead be an electrical stimulator, temperature stimulator, or other stimulator.

In certain embodiments, multiple vibratory motors create resonance or diphasic amplification. Resonant or diphasic amplification patterns may be advantageous because they may create unique vibratory patterns that would be difficult to achieve with a single vibrating source, and they may create amplification in vibratory power that exceeds the capability of a single motor. Such amplification may be useful in the case of certain electrical power or space constraints. Resonance or diphasic amplification created through the use of multiple vibratory sources may employ different sources including rotary motors, linear motors, and piezoelectrics. The combination of multiple sources may create a large range of customizable and selectable resonant patterns. Further, motors of different sizes and/or power can be used to create multiple resonant frequencies to amplify the vibration effect.

Multiple, isolated and independent motors may combine to produce diphasic amplification or resonant patterns and/or may simulate macroscopic motions. Transitions between motors are smoother with sine wave than square wave. Optimizing the timing and the amplitude of the motion during transition improves the "organic" feel of the stimulation. Preferably, multiple small motors are used to provide easily-differentiated stimulation and simulation of macroscopic motion. Small eccentric motors placed on edge provide a focused vibration point, which promotes differentiation among several vibration sources. Slower vibration transitions promote differentiation among several vibration sources as compared to more rapid transitions.

In certain embodiments, devices provide macroscopic motion in addition to, or instead of, simulating macroscopic motion. In certain embodiments, the controller is designed to map the user's motions on a control surface to the tissue-contacting surface of the stimulating part of the device. By pressing their fingers on the control surface, the user can create various levels of pressure a vibration in the corresponding location on the tissue-contacting surface. As the user moves their fingers across the control surface and optimally desired way, a sequence of motions, pressures, vibrations, and/or stimuli that mimic these actions are created on the tissue-contacting surface. These movements and inputs can be stored either locally on the device or a controller level and played back when desired to create desired effect without requiring the user to repeat their input pattern.

Figure 2A:
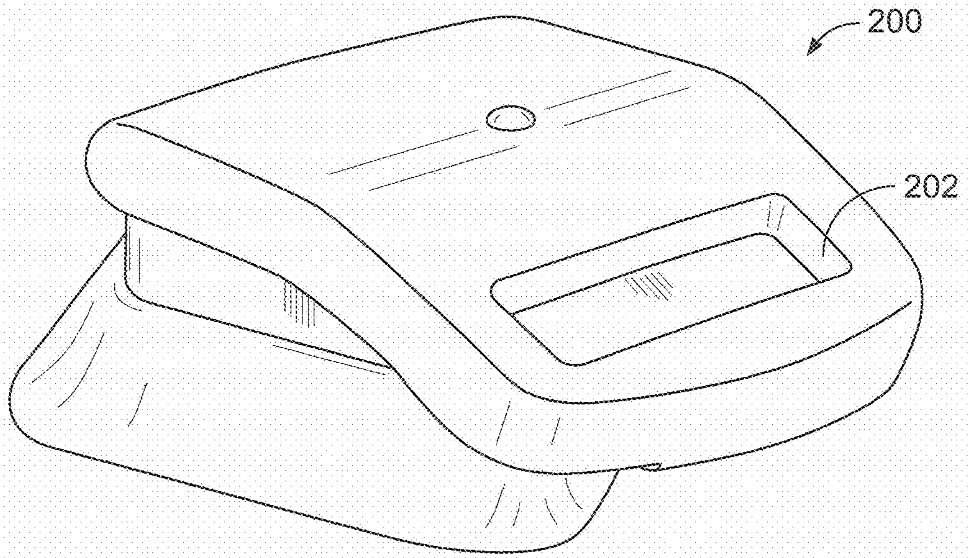
FIGS. 2A and 2B illustrate views of a device and a controller according to an embodiment of the invention.
Figure 2B:
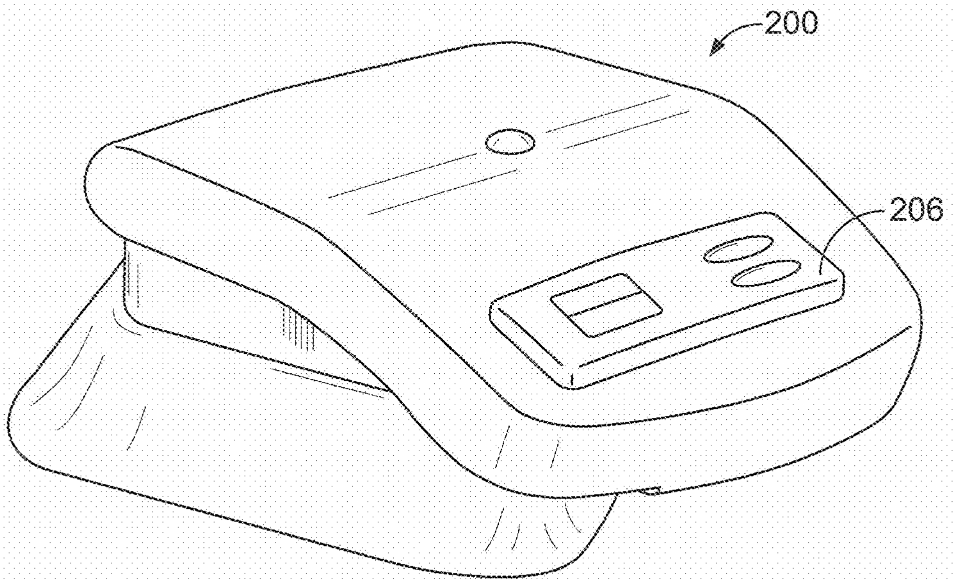

In certain embodiments, a remote controller is a controller configured to send radio-frequency signals to the device worn by the user. The controller may be sized similar to a key fob remote control commonly associated with automobiles. A key fob styled remote can include several buttons capable of controlling the full range of functions of the device discussed herein. FIGS. 2A and 2B illustrate a key fob styled remote controller 206 and device 200, which includes a complementary housing space 202 such that the remote 206 can be docked with the device and housed there when not in use or even when in use. In general, the controller circuitry can include a circuit board, amplifiers, radio antennae (including Bluetooth antennae).

Devices using low power Bluetooth or other radio antennae may experience dropped connections when the remote/device pair is separated by distance or by a physical obstruction (such as a user's or partner's body). In such cases, it is desirable for the device to remain operating under its pre-drop operating conditions while the remote attempts to automatically pair again with the device. Said differently, it is undesirable to require the user or partner to have to manually re-establish the Bluetooth pairing between the remote and the device if the pair connection is lost during device use. And, it is undesirable for the device to cease operating under its existing pre-drop conditions if a pair connection is lost. Thus, certain remotes are configured to automatically re-establish the pair connection with the device without requiring user intervention.

In situations where the remote automatically re-establishes the pair connection with the device, it can be important for the remote to query the device for the current device operating conditions. That is, since the device has maintained a state of operating conditions when the pairing was lost, it is desirable that the remote not interrupt the device operating conditions when the pair connection is re-established. As a counter example, in some Bluetooth pairings, after the pair connection is established the "master" controller will send a reset signal to the "slave" device. Such a reset would be undesirable in the circumstance where a device is operating under a given set of parameters, patterns, or programs because those parameters, patterns, or programs would be interrupted by the reset signal. Such an interruption could be detrimental to the user experience.

Some of the embodiments of the device deliver suction to engorge and stiffen the tissues and vibration to provide stimulation to the region. In other embodiments, the device delivers suction to engorge and stiffen the tissues and electrical or neural stimulation provides stimulation to the region. In other embodiments, warming or cooling is applied, including light or infrared energy (e.g., near infrared light emitting diodes), instead of vibration or electrical or neural stimulation or in combination with those stimulation types. The stimulation source preferably is in intimate contact with the tissue to optimize energy transfer.

The mounting of the vibration sources may also allow for isolation so that there is spatial differentiation between sources and minimal diffusion of vibratory energy to adjacent structures in the device or tissue. Mounting stimulators on a flexible membrane which travels with the tissue as it becomes engorged with suction may accomplish these goals. However, the membrane should have a direct path between the suction source and tissue—if there is no path the amount of suction delivered will be significantly lower. Placing holes or slits in the membrane may allow for sufficient vacuum and energy transfer. However, holes or slits are placed in the membrane may allow fluid from the tissues to travel through the membrane into the interior vibration source region of the device.

Figure 3:
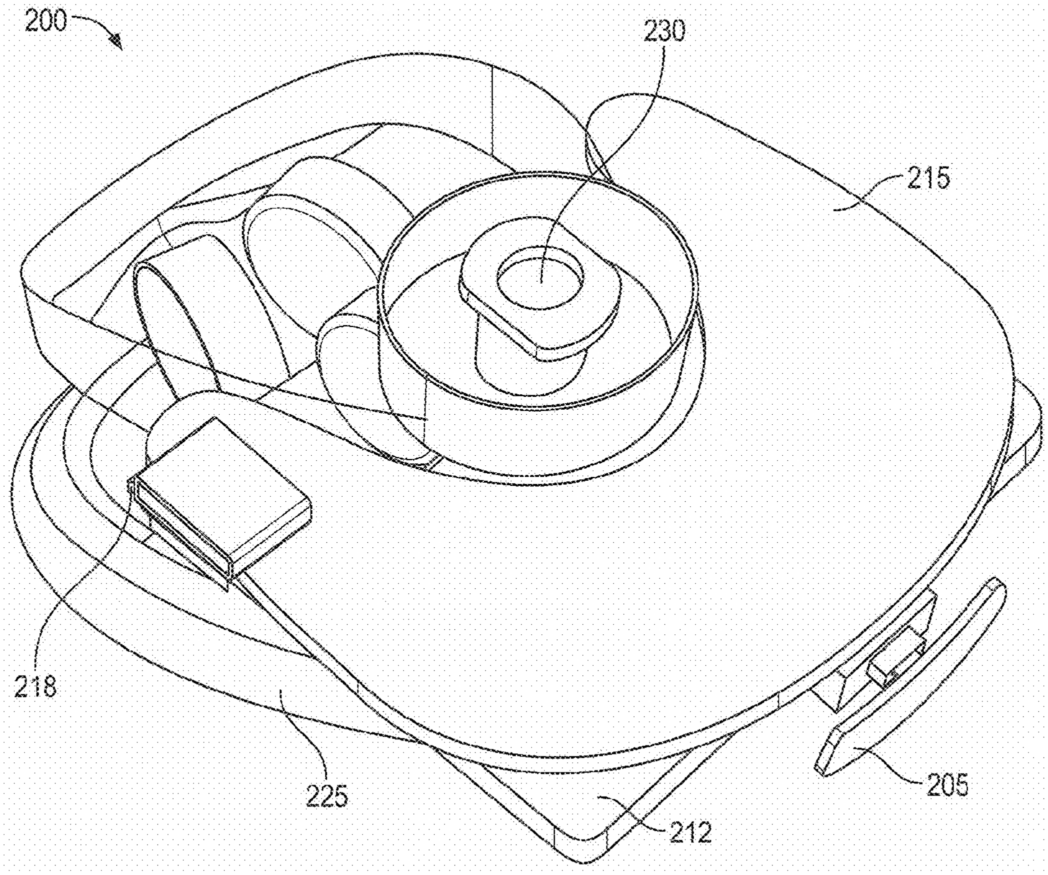
FIG. 3 illustrates a view of a device according to an embodiment of the invention.

FIG. 3 depicts a view of a device 200 with the outer housing removed. Controller block 215 (or circuit board) is housed underneath the outer housing and between suction port 230 and activation button 205. Activation button 205 is, of course, operably connected to controller block 215 as is I/O port 218. I/O port 218 can plug into an interface cable (or an interface port in a holder) that can be used to program and/or charge the device. Battery 212 is underneath controller block 215.

Miniature coin-style vibratory motors having an eccentric mass are used in certain embodiments. Generally speaking, coin-style motors require larger masses and higher power in order to increase the stimulating force delivered to tissue. Thus, the stimulating force in eccentric motors is a function of mass, and more power is required to drive that mass. In certain embodiments described herein, despite the relatively high mass and relatively high power of the motors the devices can provide spatially-differentiated vibration via the isolation structures and methods described herein. Even when the motors are positioned relatively close together to provide a close fit to the clitoris, embodiments described herein can provide substantial vibrational isolation and provide the user with a spatially-differentiated stimulation experience.

In certain embodiments, modified voice coils are used as the stimulators. As described above, voice coils can achieve high amplitude with low voltage and are smaller size than miniature coin style motors. Voice coils can be modified to include a mass attached to the membrane driven by the electromagnetic field. Advantageously, such mass-bearing voice coils retain the desirable properties of voices coils, including rapid response time, independent control of frequency and amplitude, high acceleration, high precision force control, and relatively low power consumption.

Embodiments of the device may have variable suction controlled by the user or another remote controller. A user may remotely select a pressure and the device will change to that pressure within seconds. The device may include an onboard pump that maintains suction and/or goes up/down from that initial established suction. Certain diaphragm pumps may be used as onboard pumps. Further, the motor driving the diaphragm pump may be used to produce vibratory motion. In certain embodiments, the onboard pump can be a modified voice coil designed to mimic the action of a diaphragm pump. The onboard pump can alternately be made with using a voice coil actuator that moves a membrane in a sealed and valved chamber.

In embodiments using an onboard pump or in embodiments using a remote pump, the suction may be programmed to complement the vibratory motion of the motors or the macroscopic motion of stimulators in the device. The algorithms described herein to drive vibration are adapted to vacuum pump system to provide fast response times and physically differentiable levels of suction to the clitoris. Further, certain embodiments use simultaneous or sequential suction waveforms or algorithms and vibration waveforms or algorithms to amplify the effect of the device.

In some embodiments of the device and method, variations in the stimulation parameters are particularly useful in providing the desired results in a user. For example, the stimulators can be varied between a high power and/or a high frequency level and a comparatively lower power and/or lower frequency setting. In the case of coin cell type stimulators, power and frequency are coupled such that driving the stimulator at higher frequency of oscillation also drives the stimulator at a higher power. To achieve the preferred variations in stimulation, the coin cell type stimulators can be switched between a high power threshold and a low power threshold. In the case of voice coil type stimulators, power and frequency can be decoupled such that a given power of stimulation can be driven at any frequency. Without being bound to a specific mechanism or mode of action, it is believed that comparatively large variations in the power or intensity of the stimulation will produce as desirable user experience.

One of the advantages of embodiments of the invention with multiple stimulators and suction patterns is that different parts of the anatomy can be stimulated at different frequencies. For example, different parts of the frenulum can be stimulated at different frequencies. It is generally understood that different nerve types will be stimulated to a different degree at a given frequency and that different nerves are more fully stimulated at different frequencies. One of the advantages of certain embodiments is the capability of delivering the appropriate frequency and intensity stimulation and/or suction to the different parts of the vaginal anatomy. For example, with the three stimulators positioned as shown the center stimulator primarily stimulates the glans of the clitoris and the right and left stimulators stimulate the right and left crus, respectively, (and/or frenulum) of the clitoris. The device can also enable the user to select and/or tune the desired frequency for their anatomy and nerve distribution, thereby customizing the user experience.

In certain embodiments, it is desirable to release suction during use. For example, the edge of the suction cup could be pulled back, squeezed, or manipulated to create a leak path. Further, a valve in line with the suction tube that can be manually manipulated by the user to release suction. In embodiments using an onboard suction pump, the pump can be configured to include a constant leak path that the pump overcomes—therefore, if the pump stops the device will automatically release. Still further, the device can be configured with a button that the user presses which opens a valve in the pump to release suction. Still further, the valve needed for the suction pump could be normally open. When power is supplied, the valve closes, completing the seal. However, if power goes out, the valve will open and the device will release automatically.

Certain embodiments of the present invention are designed and configured to increase blood circulation in vaginal tissue to promote engorgement to the clitoris and external genitalia while simultaneously applying stimulation to the clitoris and/or other vaginal tissue. The clitoris is a sexual organ that is filled with capillaries that supply blood to a high concentration of nerves. Certain embodiments increase blood flow to stimulate the clitoris and enhance a woman's sexual response.

In women wishing to maintain sexual wellness or be satisfied, methods and devices of certain embodiments can maintain or intensify: (i) genital sensation; (ii) vaginal lubrication; (iii) sexual satisfaction; (iv) sexual desire; and/or (v) orgasm.

Certain embodiments of the invention are designed and configured to be a wearable device designed to increase sexual satisfaction. Certain embodiments of the invention are designed and configured to be used as a "conditioning" product, to prime the user before a sexual event. Certain embodiments can be: used to help a woman prepare her body in advance of a sexual experience, typically with 5-30 minutes of use prior to sex; worn during a sexual experience with a partner, including intercourse; used by a woman alone for recreational purposes to reach orgasm; used as a regime, typically used a few minutes every day, to help facilitate a more intense and pleasurable experience during intercourse with or without a partner; or used over time to help train the body to achieve a better natural sexual response.

Figure 4A:
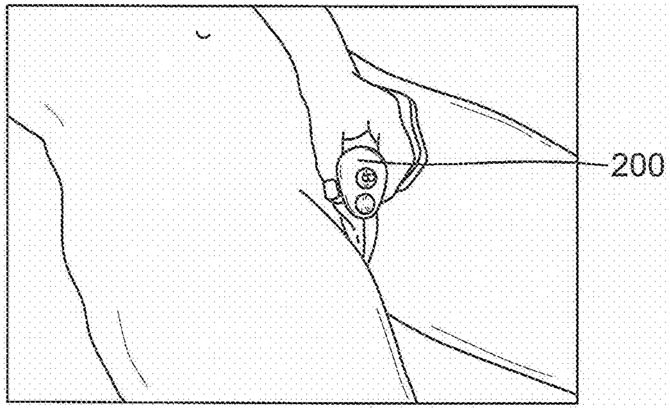
FIGS. 4A through 4E illustrate use of various embodiments of the invention.
Figure 4B:
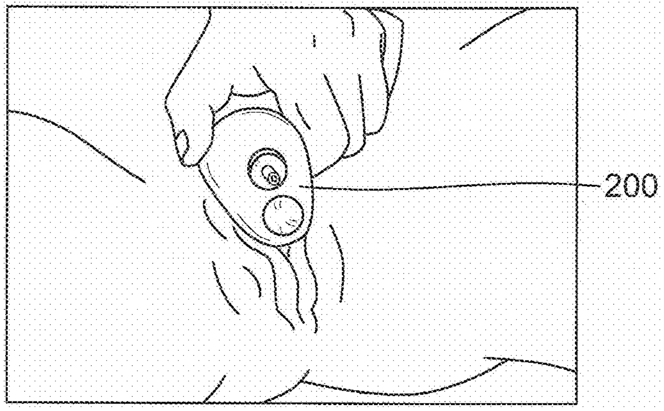
Figure 4C:
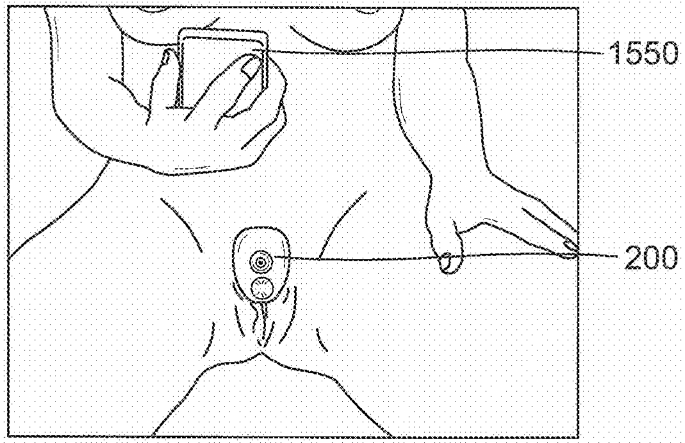
Figure 4D:
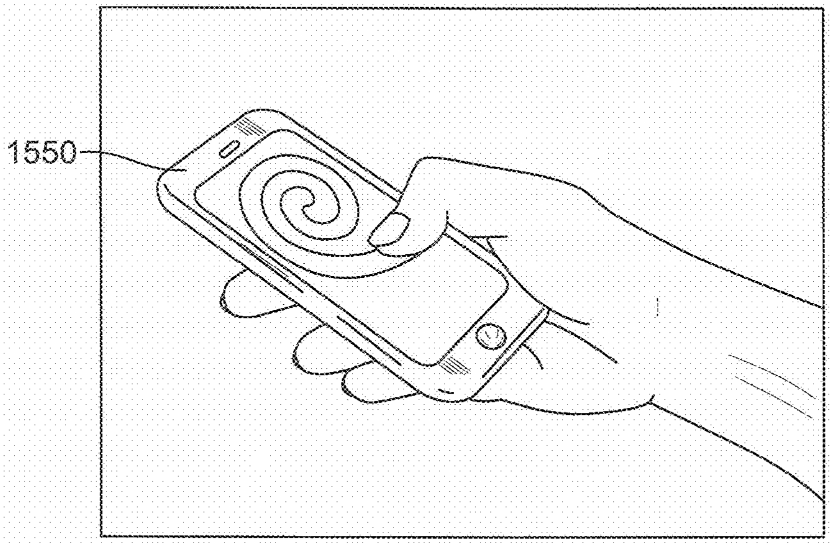
Figure 4E:

The device 200 is placed over the clitoris (FIGS. 4A-4B) by a woman or her partner. Gentle suction allows the product to stay in place (so it can be completely hands free once placed), although it can be quickly and easily removed as desired. A woman can sit, stand up and walk around while wearing the device 200. As shown in FIG. 4C, a small remote control 1550 or smartphone "app" is used to adjust the device's vibration intensity and unique stroking patterns (such as the counter-clockwise movement pictured in FIGS. 4D-4E). The sequence can be customized in advance and "playlists" can be created. Once in place, the device 200 provides quiet, hands-free sexual stimulation to the clitoral region, working with a woman's body to help improve sexual response. Certain embodiments are small (about 1.5 inches long by about 1 inch wide), quiet, waterproof and discreet. The product is latex-free, hypoallergenic and washable with soap and water. It is quick and easy to place on the body, and can easily be removed. It may be worn under clothing without anyone knowing the user has it on. Since it is a hands-free product, the user can easily move around, stand or walk while wearing the device for a few minutes a day while doing something else to help a woman's body maintain a higher level of sexual responsiveness.

Figures 5A, 5B, 5C:
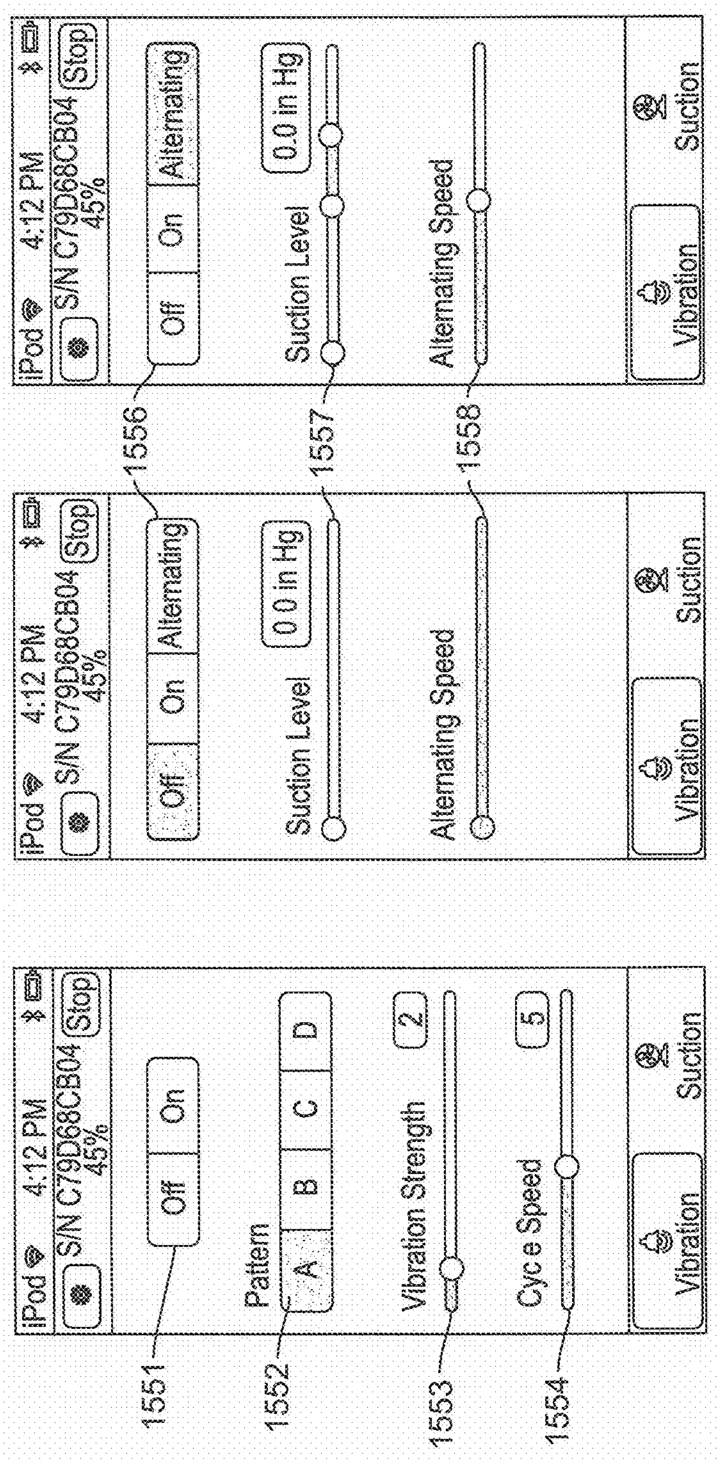
FIGS. 5A through 5C illustrate user interfaces for a smartphone-type controller.

FIGS. 5A through 5C illustrate user interfaces for a smart remote controller 1550. These user interfaces provide means for controlling vibration and suction patterns, including pre-loaded patterns, user-configurable patterns, or combinations thereof. FIG. 44A illustrates a user interface including a vibration on/off button 1551, a vibration pattern selector 1552, a vibration strength selector 1553, and a vibration cycle speed selector 1554. The vibration strength selector 1552 and vibration cycle speed selector 1554 are each shown with a numeric indicator in addition to a slider. The vibration pattern selector 1552 can be loaded with pre-loaded patterns or it can be used to store user-configurable patterns. The user interface provides an intuitive and easy-to-operate means for controlling the vibration and suction patterns of the device.

FIGS. 5B and 5C illustrate a user interface including a suction on/off button 1556, a suction level selector 1557, and a suction alternating speed selector 1558. The suction on/off button 1556 also includes an "alternating" suction setting. FIG. 5B illustrates that when the suction on/off button 1556 is in the "off" or "on" position, the suction level selector 1557 has a single slider point and the suction alternating speed selector 1558 is not available to use. When the user sets the suction on/off button 1556 to "on," the suction level selector 1557 can be used to set a suction level on the device and that suction level can be numerically displayed in units such as "in Hg."

FIG. 5C illustrates a user interface in which the suction on/off button 1556 has been set to "alternating." In the "alternating" mode, the suction level selector 1557 has two slider points and the suction alternating speed selector 1558 is available. The "alternating" mode allows the user to set a primary suction level with the first slider point and a higher suction level with the second slider point. The device can then alternate between these two suction levels at a specific alternating speed that the user sets using the suction alternating speed selector 1558. Thus, the user can control both the difference in suction levels and the speed at which the device alternates between those two suction levels. Further, the user interface can contain a means for the user to store the two suction levels and the suction alternation speed. The user interface can include pre-loaded suction alternation levels and speeds, user-configurable suction alternation levels and speeds, or combinations thereof.

Figure 6:
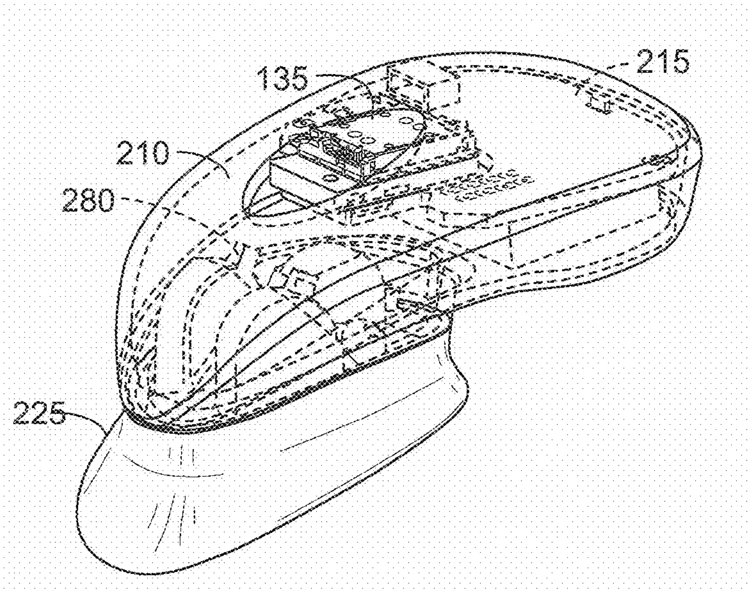
FIG. 6 is a perspective, phantom view of an integrated device.

Referring to FIG. 6, the device body 210 is illustrated to provide a view of the interior of the device body 210. The vibratory motors 280 are positioned within structures in single molded piece 22 such that the stimulation from the motors can be efficiently propagated to tissue, and portions of the vibratory motors 280 are also accessible to be connected to controller block 215. In this case, controller block 215 is illustrated as a printed circuit board. An onboard pump 135 is also positioned within device body 210. The onboard pump 135 is in fluid communication with the suction chamber to provide suction within that chamber and is also in fluid communication with an exhaust port. The exhaust port is an outlet for air or fluid pumped out of the suction chamber and an inlet for air to the suction chamber when suction is reduced. In some embodiments, the onboard pump 135 sends air pumped from the suction chamber across heat-generating elements within the device body 210 before reaching the exhaust port. Such airflow can help dissipate heat and provide safe and reliable use of the device.

In some embodiments, heat generation in the device can be monitored using a component such as a thermistor. Thermistors can be positioned within the device body 210 or be integral to the controller block 215. When the thermistor detects a threshold temperature, it can turn off power to the device and/or vent external air into the device to help the cool the device and then release suction.

In some embodiments, the onboard pump is controlled by the controller block via a closed feedback loop. That is, the controller block is configured to maintain a target pressure, which can be set by the user or can be loaded as part of a pre-programmed suction algorithm. To do so, the controller block reads real-time data from an onboard pressure sensor that is configured to monitor pressure (negative pressure in the case of suction) within the suction chamber. Based on the real-time data, the controller block can engage the onboard pump to draw more suction within the suction chamber or it can engage a check valve in fluid connection with the exhaust port to vent air into the suction chamber. In typical operation, after the device has generated sufficient suction to seal it in place on the user the controller block with periodically engage the onboard pump as suction is slowly lost through leakage.

Certain embodiments of the invention include device and methods to maintain or intensify female sexual wellness and female sexual pleasure. The methods naturally enhance a woman's own sexual response. A woman will enjoy sexual intimacy and feel confident in her body's ability to respond to sexual stimulation.

In certain embodiments, the system includes a vacuum reservoir. That is, the system includes a chamber that is capable of holding negative pressure that can be applied to the suction chamber of the device through a valve system. During initial attachment, after achieving the desired level of suction in the suction chamber, such as with an on-board pump, the vacuum source continues to run to supply the vacuum reservoir with excess negative pressure. The on-board pump can stop running, and if a small leak develops the negative pressure in the vacuum reservoir can supply suction to the suction chamber until it is exhausted, and then the pump can turn back on to replenish the reservoir and suction chamber and then stop running again. One advantage of the vacuum reservoir is that the desired level of suction can be maintained while having the suction source operate comparatively less than a system without a vacuum reservoir.

Systems described herein can be equipped with sensors and sensing capabilities. The data collected from sensing can be used in a variety of ways, such as display to the user and/or feedback to the device control systems. Sensed parameters include tissue temperature, tissue impedance, blood flow, tissue turgidity and/or engorgement, heart rate, and blood pressure. The data can be represented on the user control device, such as a smartphone. The data can be represented graphically and/or numerically and can be mapped over a visual representation of the anatomy. In a sense, the displayed data can be an "arousal meter" that provides information to the user. Further, the state of the user's arousal can be used to provide a biofeedback loop to control the device. For example, the user can set an arousal level on the device prior to use and the device can monitor the user's arousal state. By sensing the arousal state, the device control systems can increase or decrease stimulation to meet the user-set state.

In many of the embodiments described herein, it can be desirable to apply therapeutic energy to clitoral and/or vulvar tissue, such as light energy or electromagnetic energy. Certain light frequencies can decrease tissue inflammation and certain light frequencies can increase local blood flow.

In many of the embodiment described herein, it can be desirable to provide ambient sounds via the device or system. Ambient sounds can be soundscapes that promote feelings of well-being and/or arousal in the user. Additionally, the ambient sound can be a "white noise" that provides a relatively constant background sound and thereby masks or de-emphasizes sounds made by the device during device operation. To that end, the device or system could include an active noise cancellation system.

Figure 7:
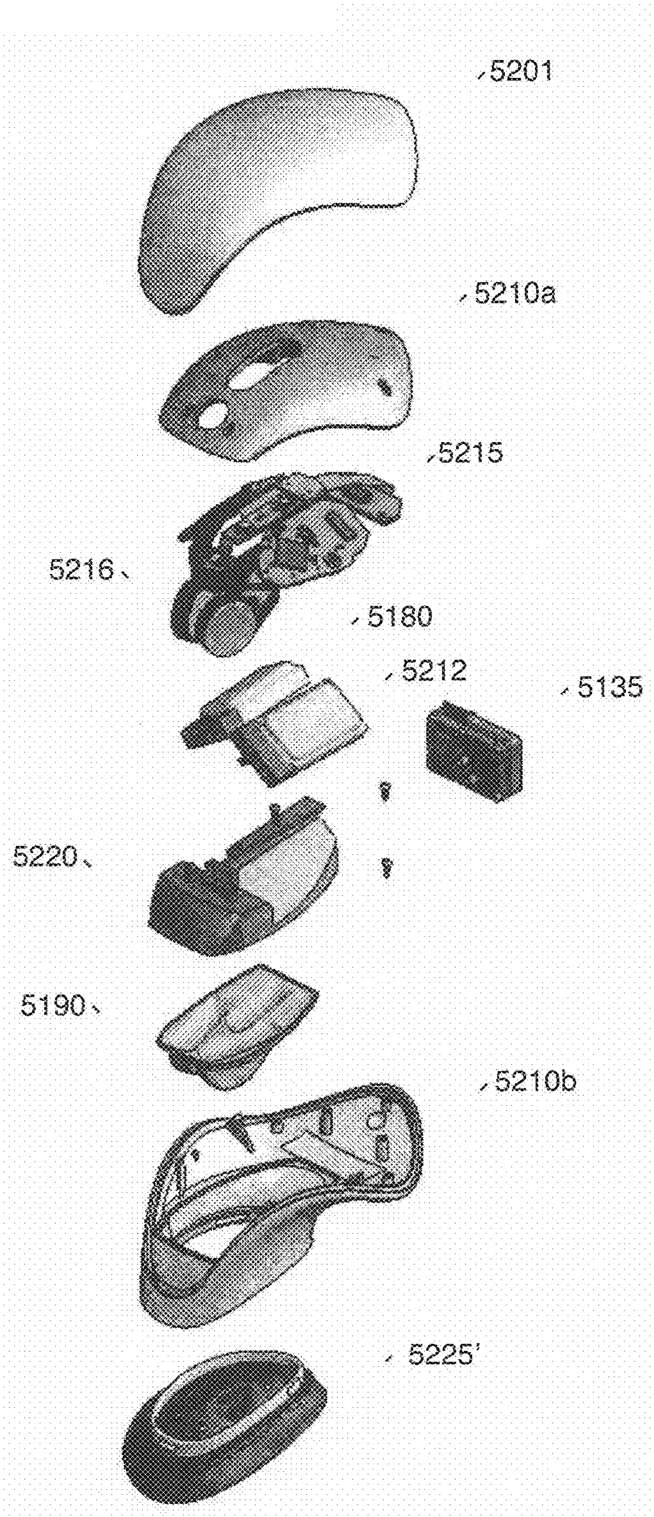
FIG. 7 depicts an exploded view of a device according to aspects of the invention.

FIG. 7 depicts an exploded view of a device according to aspects of the invention. A cover 5201 can be affixed to upper device body 5210*a*. The cover 5201 includes cosmetic features, giving the device visual and tactile appeal. For example, the cover 5201 can be formed from a thermoplastic elastomer, a thermoplastic polyurethane, a silicone polymer, or combinations thereof. The cover 5201 can have various surface textures, including a matte-style texture or other "soft-touch" textures. The cover 5201 can be formed with various patterns and colors, including liquid film printing on the inside surface of the cover 5201 to provide visually pleasing color depth. Of course, other finishes including glossy finishes, slick textures, grippy textures and many others are possible for cover 5201. In some embodiments, the cover 5201 can be a comparatively rigid part, including having rigidity comparable to the rigid parts of the device body.

The cover 5201 can also provide a seal for the assembled device body, which consists of the device body cover 5210*a* and lower device body 5210*b*. The device body cover 5210*a* is configured to attach with the lower device body 5210*b* and together they form a device body that contains device components, including the pump 5135, the controller block 5215, and battery (or batteries) 5212. The components housed between the device body cover 5210*a* and the lower device body 5210*b* are moisture sensitive. Thus, the cover 5201 should provide a fluid tight seal for the assembled device body. Both the device body cover 5210*a* and the lower device body 5210*b* can be formed by various methods, including injection molding, and from suitable materials, such as polycarbonate. The components housed inside the assembled device body include a controller block 5215, which in FIG. 7 is depicted as a custom shape formed of printed circuit boards and associated flexible circuit boards.

Still referring to FIG. 7, a suction housing 5220 is shown as fitting between the device body cover 5210*a* and the lower device body 5210*b*. The suction housing 5220 is sealed against the lower device body 5210*b* to form a vacuum tight seal. The suction housing 5220 forms the upper boundary of a suction chamber for stimulating tissue. The batteries 5212 can be placed between the upper surface of the suction housing 5220 and the controller block 5215. The active stimulators 5180 are located underneath the suction housing 5220 and positioned within the motor membrane 5190. When fully assembled, the lower portions of the motor membrane 5190 are in contact with the motor recesses 5227'*r* of the removable flange assembly 5225'.

Figure 8:
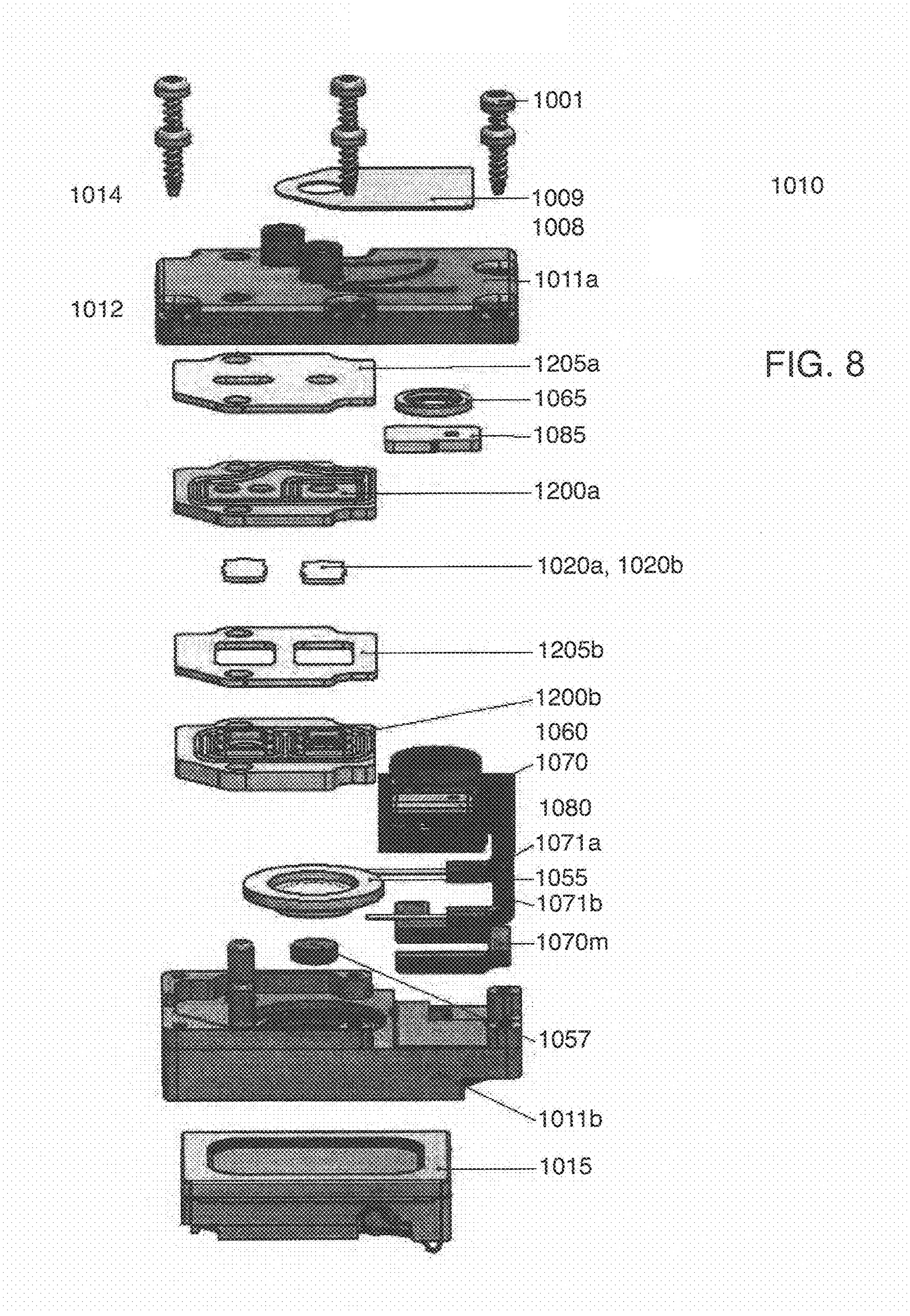
FIG. 8 illustrates an exploded perspective view of an embodiment of a miniature pump.

FIG. 8 illustrates an exploded perspective view of an embodiment of a miniature pump 1010 that is suitable for use in the devices disclosed herein. The miniature pump 1010 includes an actuator 1015, which can be an electromagnetic voice-coil type actuator such as those commonly used in mobile phones and other electronic devices. Attached to the actuator 1015 is the lower body 1011*b*, which contains the diaphragm assembly as described previously herein. FIG. 8 specifically depicts certain elements of the diaphragm assembly, including the magnet 1057 and the diaphragm 1055. The lower body 1011*b* and the lower valve assembly body 1200*b* together form the diaphragm chamber as described elsewhere herein. FIG. 8 further illustrates lower body 1011*b* supporting the control board 1070 via the control board mount 1070*m* and control board wires 1071*a*, 1071*b* extending from the control board 1070, providing electrical connectivity to the electromagnetic features of the diaphragm assembly. Also present on the control board 1070 are the sensor 1080, which has the sensor gasket 1085 forming a seal between the sensor 1080 and the upper body 1011*a*, and the blow-off valve 1060. The blow-off valve diaphragm 1065 is illustrated in FIG. 8, while the upper sections of the blow-off valve, including its exit port, are not specifically pictured.

Still referring to FIG. 8, lower valve assembly body 1200*b* is attached to the upper surface of the outer ring of diaphragm 1055. The lower valve assembly body 1200*b* can include the valve recesses, inlet ports, and sealing surfaces necessary to provide the valve action described herein. These features can be integrally formed into the lower valve assembly body 1200*b*, such as by injection molding a unitary part, they can be formed from multiple molding process, or they can be fabricated into the lower valve assembly body 1200*b* by cutting or machining or the like. The lower valve assembly gasket 1205*b* is placed between lower valve assembly body 1200*b* and upper valve assembly body 1200*a* and provides a fluid tight seal to the valve chambers. The inlet valve 1020*a* and outlet valve 1020*b* can float within the valve chambers and function as described elsewhere herein.

Again still referring to FIG. 8, upper valve assembly body 1200*a* is similar to lower valve assembly body 1200*b* in that it can include the valve recesses, inlet ports, and sealing surfaces necessary to provide the valve action described herein and such features can be formed in the same variety of ways described for lower valve assembly body 1200*b*. Further, the fluid flow paths necessary to provide connections among the valve chambers, pressure sensor, and blow-off valve can be formed in upper valve assembly body 1200*a*. The upper valve assembly gasket 1205*a* can form the upper boundary of some of these flow paths and provides a seal between the upper valve assembly body 1200*a* and the upper body 1011*a*. The upper body 1011*a*, in turn, can also have flow paths, which in FIG. 8 are depicted as upper body channels 1008. The upper valve assembly gasket 1205*a* and the upper body seal 1009 for the lower and upper boundaries, respectively, for certain flow paths. Further, the cutouts in the upper valve assembly gasket 1205*a* provide a fluid connection to the inlet port 1012 and outlet port 1014 on the upper body 1011*a*. Screws 1001 are used in the final assembly of the miniature pump 1010, but of course other methods of securing the upper body 1011*a* to the lower body 1011*b* can be used.

The flow paths in the upper body 1011*a* provide several connections, such as: (1) a connection between the blow-off valve and the inlet port of the miniature pump; (2) a connection between the blow-off valve and the outlet port of the miniature pump; and (3) a connection between the pressure sensor and the suction chamber.

The term "blow-off" valve as used herein refers generally to a type of valve used to control or limit the pressure in a system or vessel. Such valves may also be known as relief valves, safety valves, and the like, and certain embodiments herein encompass such valves regardless of how they are named.

The blow-off valve, the sensor, and the control board work together in a closed loop control system for monitoring and adjusting the performance of the miniature pump. In one example, the closed loop control systems can be programmed to maintain a level of negative pressure within the diaphragm chamber. That is, the sensor continuously monitors the pressure level in the diaphragm chamber and provides that data to the control board. The firmware (or software) on the control board can compare the data to the programmed pressure level and then send power to the actuator to drive the miniature pump to increase the pressure or send a signal to the blow-off valve to release negative pressure. In another example, a pre-programmed or user-selected suction profile can be generated using the closed loop control system. That is, rather than seeking a set level of negative pressure, the closed loop control system seeks a time-dependent pattern of pressure levels by continuously comparing the negative pressure level in the diaphragm chamber with the time-dependent level specified in the profile. The blow-off valve or the pump can then be activated as needed.

In another example, the closed loop control system can help optimize the efficiency of operation and reduce noise levels. In this example, the firmware uses a lookup table to find optimal operating conditions for the miniature pump at a given level of negative pressure. At a given pressure the miniature pump may operate most efficiently at a certain power signal profile. That is, a particular shape of the signal waveform (e.g., the amplitude and frequency of a sinusoidal signal) may allow the miniature pump to operate more quietly than another similar shape at a given pressure. Generally, noise in the miniature pump is generated by the diaphragm hitting the walls of the diaphragm chamber and by the valves hitting the walls of their valve recesses and offsets. By calibrating the position of the diaphragm and valves at given power levels and pressure levels and cross-referencing those positions against power and pressure levels in a lookup table accessible to the firmware, the miniature pump can be operated in a way that reduces or eliminated valve and/or diaphragm noise. Further, reducing or minimizing diaphragm and valve noise increases the efficiency of the miniature pump since less energy is lost to the pump body through collisions between the valves and/or diaphragm and the pump body.

Another advantage of the closed loop control system is that the blow-off valve can be activated under certain conditions. For example, if the negative pressure exceeds a certain level, the firmware can activate the blow-off valve to allow air into the diaphragm chamber. As another example, if the valve temperature rises above a certain level (as detected by a temperature sensor integrated into the miniature pump and in communication with the control board), the firmware can activate the blow-off valve.

Generally, the control and sensing components of the miniature pump can reside within the pump housing or can be remote from the pump. That is, a processor and sensor can be located away from the actual pump body and still be able to provide the sensing and control features described herein. Also, the blow-off valve may be located remotely from the pump body provided it has the fluid connection necessary to provide the pressure relief performance. Thus, the closed loop feedback system can exist in a system of physically separate components that are functionally interconnected.

Figure 9A:
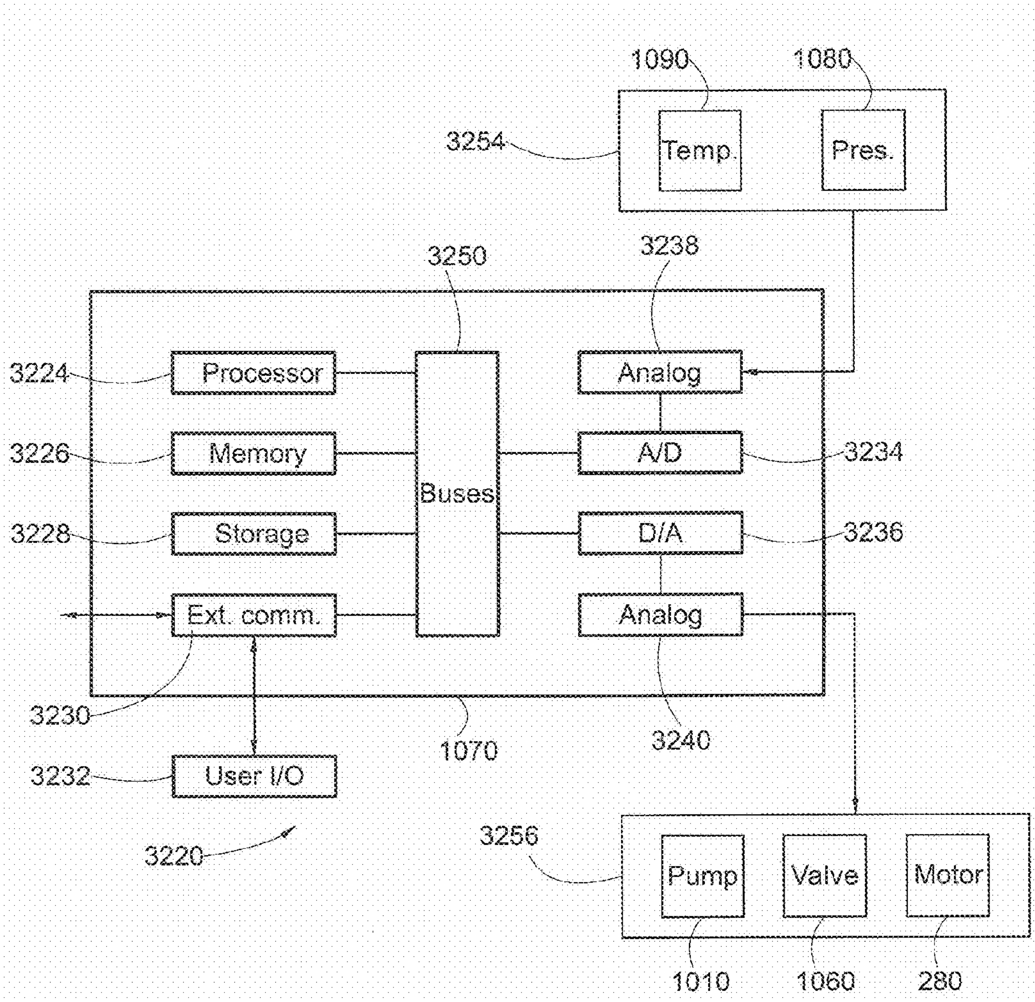
FIG. 9A illustrates a control and I/O subsystem including a number of control, storage and I/O components according to some embodiments of the present invention.

FIG. 9A illustrates a control and I/O subsystem 3220 including a number of control, storage, and I/O components according to some embodiments of the present invention. Some of the components may be part of the control board 1070, while others, such as a set of user input-output (I/O) devices 3232, sensors 3254 and active mechanical devices 3256 may be electrically connected to, but physically separated from, the control board 1070. Sensors 3254 include one or more pressure sensors 1080 and one or more temperature sensors 1090, which provide real-time indicators of pressure and temperature within the device suction chamber. Other sensors may include flow sensors, accelerometers, and others. Active mechanical devices 3256 include one or more suction pumps 1010, one or more blow-off or other valves 1060, and one or more motors 280.

In some embodiments, the control board 1070 includes a processor 3224, a memory 3226, a set of storage devices 3234, and a set of external communications interface controller(s) 3230, and analog-to-digital (A/D) converter 3234, and a digital-to-analog (D/A) converter 3236, all interconnected by a set of buses 3250. Analog circuitry 3238 is connected to A/D converter 3234. Analog circuitry 3238 includes components such as amplifiers and filters configured to perform analog processing such as amplification and filtering on analog signals received by the control board 1070 from external sensors. Analog circuitry 3240 is connected to D/A converter 3236. Analog circuitry 3240 includes components such as amplifiers configured to perform analog processing such as amplification on analog signals received from D/A converter 3236. A/D converter 3234 and D/A converter 3236 connect the processor 3224 to the blow-off valve, sensor, and diaphragm, as described below. In some embodiments, at least some of the illustrated sensors (e.g. pressure sensor(s) 1080) may be digital sensors connected to processor 3224 through a digital bus such as an I2C bus.

In some embodiments, the processor 3224 comprises one or more microcontroller integrated circuit(s) or other microprocessor(s) configured to execute computational and/or logical operations with a set of signals and/or data. Such logical operations are specified for the processor 3224 in the form of a sequence of processor instructions (e.g. machine code or other type of software). In some embodiments, processor 3224 may include multiple discrete microprocessors interconnected by a connection such as a serial bus. For example, processor 3224 may include a Bluetooth microprocessor connected to a control system-on-chip (SoC) through a Universal Serial Bus (USB), RS232, UART or other digital connection. A memory unit 3226 may comprise random access memory (RAM, e.g. DRAM) storing data/signals read and/or generated by processor 3224 in the course of carrying out instructions. The processor 3224 may also include additional on-die RAM and/or other storage.

Storage devices 3228 include computer-readable media enabling the non-volatile storage, reading, and writing of software instructions and/or data, such as EEPROM/flash memory devices. Communications interface controller(s) 3230 allow the subsystem 3220 to connect to digital devices/computer systems outside the control board 1070 through wired and/or wireless connections. For example, wired connections may be used for connections to components such as user I/O devices 3232, while wireless connections such as Wi-Fi or Bluetooth connections may be used to connect to external components such as a smartphone, tablet, PC or other external controller. Buses 3250 represent the plurality of system, peripheral, and/or other buses, and/or all other circuitry enabling communication between the processor 3224 and devices 3226, 3228, 3230, 3234, and 3236. Depending on hardware manufacturer, some or all of these components may be incorporated into a single integrated circuit, and/or may be integrated with the processor 3224.

User I/O devices 3232 include user input devices providing one or more user interfaces allowing a user to introduce data and/or instructions to control the operation of subsystem 3220, and user output devices providing sensory (e.g. visual, auditory, and/or haptic) output to a user. User input devices may include buttons, touch-screen interfaces, and microphones, among others, provided on the device housing or on a smart phone or remote control. User output devices may include one or more display devices, speakers, and vibration devices, among others, provided on the device housing or on a smart phone or remote control. Input and output devices may share a common piece of hardware, as in the case of touch-screen devices. In some embodiments, user I/O devices 3232 incorporated with the device housing include a status LED light and three user control buttons: a mode button, which can be used to switch between adjusting suction levels and mechanical stimulation levels and/or manual and autoattach modes described below, and level increase (+) and decrease (−) buttons, which can be used to adjust pump and/or motor settings. A remote control may include similar user control buttons and status light.

In some embodiments, the processor 3224 controls the positioning of the pump diaphragm by using analog circuitry 3240 to dynamically control a DC offset and a gain of a diaphragm drive signal. The offset level controls the DC bias of the pump diaphragm, while the gain controls the amplitude of a sinusoidal or other periodic signal waveform; the periodic signal amplitude and offset determine the amplitude of the excursion of the pump diaphragm from its resting position. The offset and gain may be controlled dynamically in response to measured operational parameters in order to achieve desired operational characteristics, as described below. In particular, the offset and/or gain may be changed in response to variations in pressure measured using a sensor. In some embodiments the minimum and maximum applied force, which control the excursion of the pump diaphragm, may be controlled using other two discrete parameters such as a minimum and a maximum signal amplitude.

As the pump operates over time in a given evacuation sequence, the pressure differential across the pump diaphragm generally increases. Without changes in offset and gain, the increasing pressure differential would lead to a gradual change in the resting position of the pump diaphragm. The increase in pressure difference leads to changes in the optimal offset and gain values for achieving particular pump characteristics such as maximum rate of increase in pressure difference (pumping speed), minimum current consumption (or maximum energy efficiency), or minimal noise. In some embodiments, the offset is decreased (or increased) over time to compensate for the effect of the increased pressure differential across pump diaphragm on the resting position of the diaphragm. The offset and gain values may be varied according to a pressure lookup table, and/or according to dynamically measured changes in one or more parameters of interest, such as a pressure difference (delta) observed over one pump cycle.

Figure 9B:
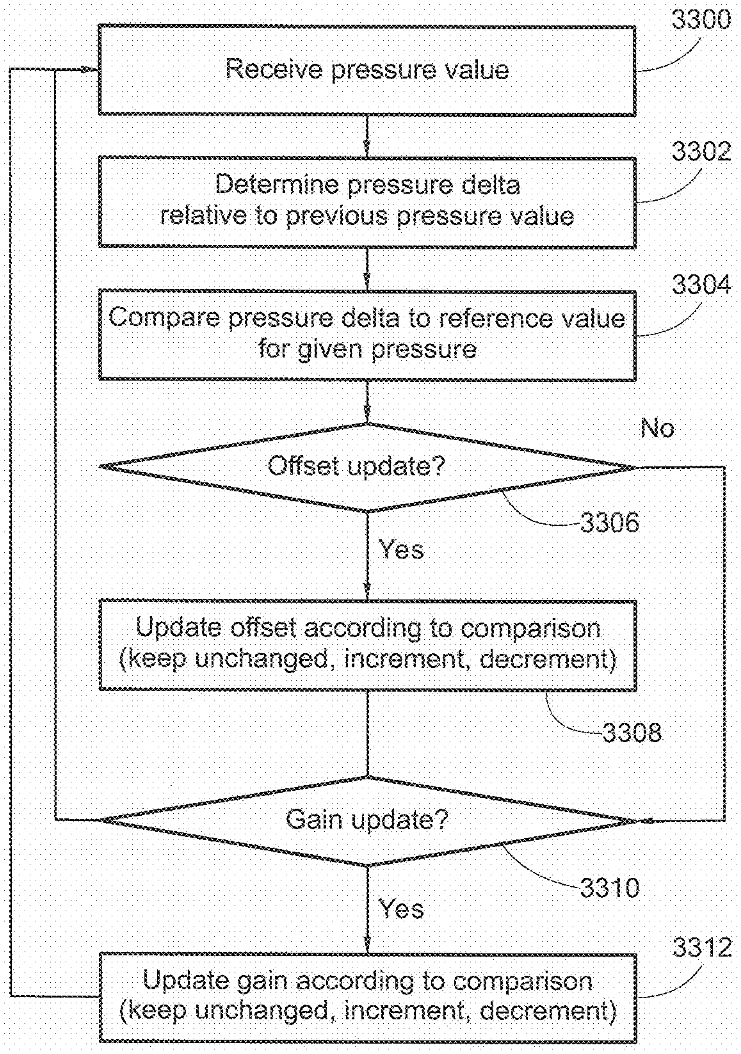
FIG. 9B shows a flowchart illustrating a number of steps performed by a processor to dynamically control a diaphragm according to pressure values measured by a sensor according to some embodiments of the present invention.

FIG. 9B shows a flowchart illustrating a number of steps performed by processor 3224 to dynamically control the diaphragm according to pressure values measured by the sensor according to some embodiments of the present invention. In a step 3300, processor 3224 receives an instantaneous pressure value measured by the pressure sensor 1080 for the current pump cycle. In a step 3302, the pressure difference (delta) relative to a previously-measured pressure value (e.g. a pressure value measured for the immediately-prior pump cycle) is determined. In a step 3304, the determined pressure delta is compared to one or more reference values, in order to determine a magnitude and/or sign of offset and/or gain adjustments to be made for subsequent pump cycles. A reference value may be equal to or otherwise determined according to a pressure delta measured for an immediately-previous pump cycle, or an expected pressure delta for a given measured pump pressure as retrieved from a calibration table or other storage. Performing such a comparison may comprise subtracting a reference value from the measured pressure delta.

In a step 3306, it is determined whether the offset is to be updated for the next pump cycle. In some embodiments, the determination whether to update the offset may be performed independently of the pressure delta comparison described above. For example, offset updates may be performed during certain blocks of cycles while gain updates are performed during other blocks of cycles, in order to attempt to separate the measured effects on pressure delta of offset and gain changes. In another example, offset and gain updates may be performed on alternating pump cycles. In some embodiments, both offset and gain updates may be performed during at least some pump cycles. In some embodiments, a determination whether to update the offset may be performed according to the pressure delta comparison described above, if it is determined that an offset change is likely to improve pump performance.

In a step 3308, the offset is updated according to the pressure delta comparison performed in step 3304. In some embodiments, updating the offset comprises incrementing or decrementing the offset by a fixed step (e.g. ±1) if it is determined that such incrementing/decrementing is likely to lead to improve pump performance on the next pump cycle.

In a step 3310, is it determined whether the gain is to be updated for the next pump cycle. Step 3310 may be performed in a manner similar to that described above for step 3306. Subsequently, in a step 3312, the gain is updated according to the pressure delta comparison performed in step 3304. In some embodiments, updating the gain comprises incrementing or decrementing the gain by a fixed step (e.g. ±1) if it is determined that such incrementing/decrementing is likely to lead to improve pump performance on the next pump cycle.

Figure 9C:
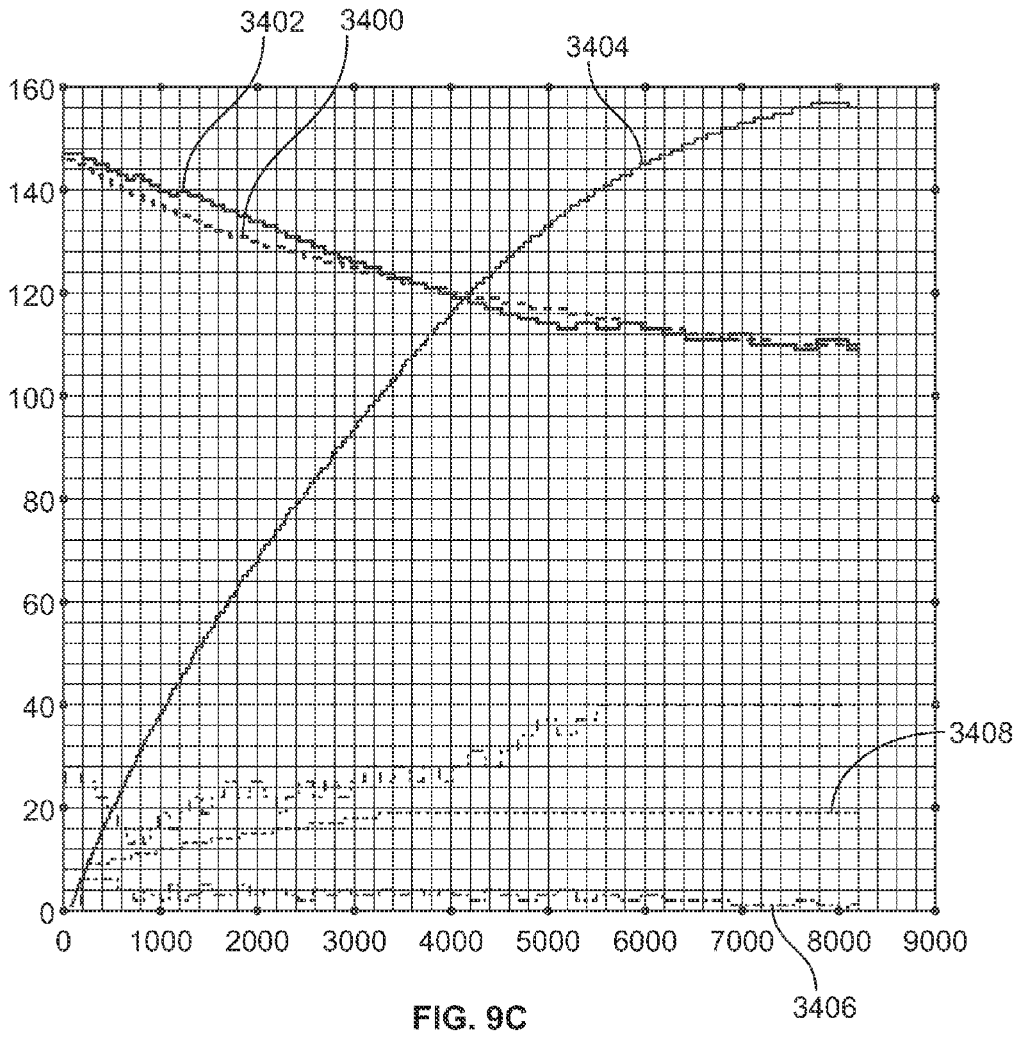
FIG. 9C illustrates an exemplary evolution over a number of pump cycles of several parameters described above, according to some embodiments of the present invention.

FIG. 9C illustrates an exemplary evolution over a number of pump cycles of several parameters described above, according to some embodiments of the present invention. The x-axis denotes time (or pump cycles), while the y-axis illustrates the various parameter values. An estimated offset 3400 represents an offset chosen according to a predetermined calibration table, independently of dynamically-measured pressure values. A dynamically-determined offset 3402 represents an offset chosen according to dynamically-determined pressure delta values as described above. A vacuum level (compression) 3404 represents the measured vacuum level, or pressure differential across the diaphragm. A gain 3408 represents a gain of the pump drive signal. A pressure delta 3406 represents the pressured delta observed over each pump cycle, i.e. effectively the derivative of the vacuum level 3404.

As illustrated in FIG. 9C, the vacuum level 3404 increases over time as the pump operates, with the per-cycle pressure delta 3406 generally decreasing over time as the pump works against an increasing diaphragm pressure differential. The gain 3408 suitable for maintaining the pump in an optimal operating regime increases over time. At each time point, a low gain leads to a suboptimal displaced volume, while a high gain can lead to a loss of efficiency and/or noise if the diaphragm collides with its housing at the end of its excursion. At the same time, the offset corresponding to an optimal operating regime decreases over time, compensating for the effect of the pressure differential across the diaphragm. The dynamically-determined offset 3402 may differ from the previously-determined (calibrated) offset 3400, for example due to differences between the individual characteristics of the pump (which determine the offset 3402) and the general pump characteristics used to generate the calibration data determining the estimated offset 3400. For example, while the general offset 3400 decreases monotonically, the dynamically-determined offset 3402 occasionally increased. Also, the dynamically-determined offset 3402 at times decreased at a different rate than the general offset 3400. Using dynamically-determined offset 3402 facilitates the manufacture of pumps using less-stringent manufacturing tolerances, as optimal pump operation is less dependent on any mismatch between individual pump characteristics and the general pump characteristics reflected in calibration data.

In some embodiments, a pump and associated control system as described above may be used to generate pressure patterns other than a monotonically-increasing one such as the one illustrated in FIG. 9C. For example, alternating pressure (suction) periods may be used by alternating periods of increased pumping (and/or decreased associated relief valve use) with periods of decreased or stopped pumping (and/or increased associated relief valve use).

Figure 9D:
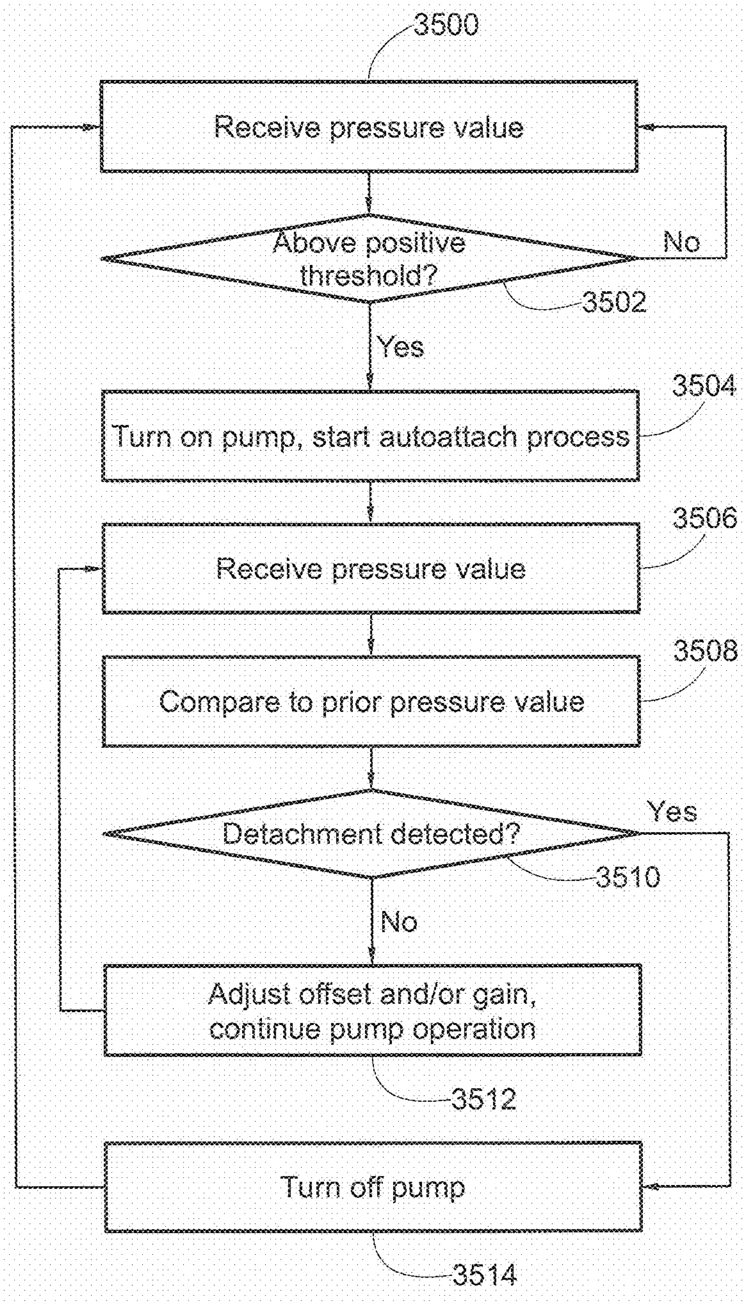
FIG. 9D shows an exemplary sequence of steps performed by a control system to implement an auto-attach mode according to some embodiments of the present invention.

FIG. 9D shows an exemplary sequence of steps performed by a control system to implement an auto-attach mode. Such an operating mode may be provided as a user-selected alternative to a manual operating mode. In the manual operating mode, the pump is started immediately in response to user input such as pressing a pump-start button. In an auto-attach mode, the pump is automatically started in response to the detection of positive pressure indicative of the establishment of contact of the sealing flange 225 (FIGS. 1A-1D) to a user's tissue. In a step 3500, processor 3224 receives a current measured pressure value while the pump is off. In a step 3502, processor 3224 compares the measured pressure to a predetermined positive threshold. Detecting a high level of positive pressure indicates that the chamber to be evacuated has been engaged and at least somewhat sealed against user tissue. If the measured pressure is not above the threshold, the process returns to step 3500. If the measured pressure is above the threshold, processor 3224 starts the pump auto-attach process by turning on the pump (step 3504). A current pressure value for the present pump cycle is received in a step 3506, and compared to a prior pressure value in a step 3508. In a step 3510, it is determined whether the measured pressure value(s) indicate that the chamber seal has been breached. For example, a sudden large drop in pressure or a return to atmospheric pressure may indicate that the suction chamber is no longer sealed. If no major loss of seal is detected, the commanded pressure is adjusted, and the dynamically tuned parameters offset and/or gain are adjusted as described above (step 3512), and the process returns to step 3506 to receive a pressure value for the next pump cycle. If major loss of seal is detected, the pump is turned off (step 3514), and the process returns to step 3500 to allow detecting a new engagement of a chamber.

In some embodiments, step 3512 may include turning on and off the pump so as to maintain a certain level of negative pressure. Step 3512 may include monitoring parameters such as the fraction of time that the pump is on or the pump pressure is low to determine whether to increase or decrease the pump's activity. The pump then self-regulates to maintain a certain level of negative pressure.

Figure 10A:
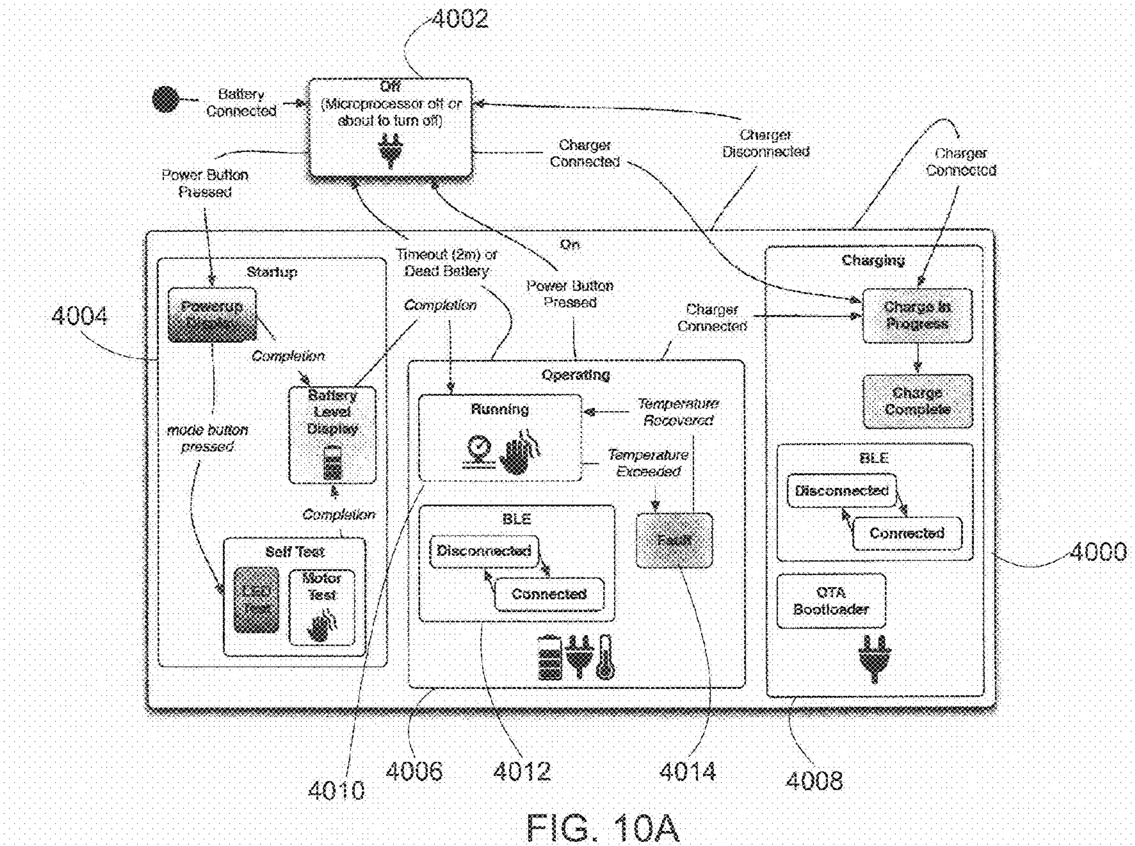
FIG. 10A shows a state diagram for an exemplary system-level finite state machine according to some embodiments of the present invention.
Figure 10B:
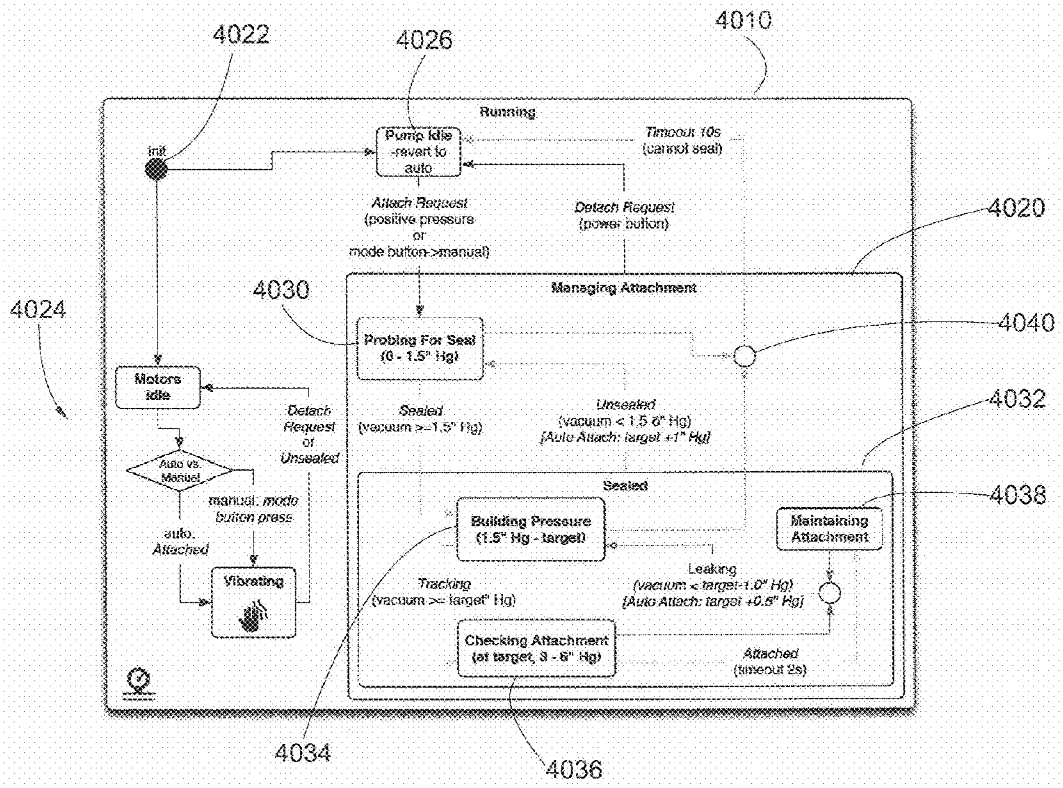
FIG. 10B shows a state diagram for an exemplary attachment-management finite state machine according to some embodiments of the present invention.

FIGS. 10A and 10B show exemplary state diagrams illustrating the operation of a finite state machine (FSM) implemented using processor 3224 according to some embodiments of the present invention. FIG. 10A shows a system-level diagram illustrating a number of startup, operating and charging states and associated state transitions, while FIG. 10B illustrates a number of operating state substates used to manage an attachment of the device, including an autoattachment process according to some embodiments of the present invention. The diagrams of FIGS. 10A and 10B include multiple hierarchical state levels, and the system may be in more than one of the illustrated states at the same time. Entry and exit to/from each described state comprises execution of entry and exit code associated with the given state and/or state transition. The exemplary pressure values illustrated in FIG. 10B are absolute values, which may correspond to negative pressure values.

As shown in FIG. 10A, processor 3224 may be in an on-state 4000 or an off-state 4002. On-state 4000 includes a startup sub-state 4004, an operating sub-state 4006, and a charging sub-state 4008. The system transitions from off state 4002 to startup state 4004 upon detection of a power button user input. Start-up state 4004 includes a powerup display state, a battery level display state, and a self-test state. The self-test state includes LED test and motor test states, in which self-tests of systems LEDs and motors are performed, respectively. The system transitions from the powerup display state to the self-test state upon detection of a mode button user input. Upon completion of powerup display and battery level display sequences, and optionally a self-test sequence, the system transitions to a running state 4010 of operating state 4006.

Running state 4010 embodies a number of operations described in detail above, and in particular a number of attachment management steps and states described below with reference to FIG. 10B. As shown in FIG. 10A, operating state 4006 further includes a remote control communication (Bluetooth) management state 4012 which manages a remote control connection, and a temperature fault management state 4014 activated in response to detection of an excessing temperature by a temperature sensor.

The system may enter charging state 4008 from off state 4002 or from on-state 4000. Charging state 4008 includes charge-in-progress, charge complete, remote control (Bluetooth) management, and over-the-air (OTA) bootloader (initialization) states.

As shown in FIG. 10B, running state 4010 includes an attachment management state 4020 used to manage an attachment of the suction chamber to user tissue through operation of the on-board suction pump. The system may enter attachment management state 4020 from an initial state 4022 through a pump idle state 4026. The system may also transition from initial state 4022 to a set of device motor management states 4024, whose operation is described above. In some embodiments, the system may operate in attachment management state 4020 and device motor management states 4024 substantially concurrently, and operations embodied by attachment management state 4020 and device motor management states 4024 may be performed substantially concurrently.

A transition from pump idle state 4026 to attachment management state 4020 occurs in response to detection of a manual or automatic attachment request/command, and triggers a start of the on-board suction pump. In manual mode, a manual attachment request comprises a user's express action to start the device pump. In auto-attach mode, an automatic attachment request is triggered by detection of a positive pressure value (relative to atmospheric/ambient pressure), which indicates that air has been trapped and compressed in the suction chamber by a user's sealing the suction chamber against user tissue.

An exit from attachment management state 4020 back to pump idle state 4026 occurs upon a timeout of a predetermined duration indicating a failure to establish a seal, as illustrated at 4040 in FIG. 10B. In some embodiments the predetermined duration may have a value between 3 and 30 seconds, more particularly between 5 and 15 seconds, and in an exemplary embodiment about 10 seconds (e.g. 9-11 seconds). A short duration may lead to unnecessary demands on the user's attention, while a long duration may lead to undesirable effects on device operation and durability, for example due to battery discharge and unnecessary heating. As described below, the sufficiency of a seal may depend on the physical seal established along flange 225 (see FIGS. 1A-1D) and the ability of the suction pump to overcome any leaks over a time interval before an exit to the pump idle state is triggered. In some embodiments, the sufficiency of a seal may be evaluated according to different measured parameters or a different analysis, for example by explicitly evaluating the time-dependence (e.g. derivative) of measured pressure, and/or explicitly tracking a seal-quality function dependent on pressure and time.

As shown in FIG. 10B, the system enters a probing-for-seal state 4030 in response to receiving an attachment request. An exit from the state occurs to a sealed state 4032 if a seal has been detected, or through timeout to pump idle state 4026 if a seal has not been detected, as illustrated at 4040. In some embodiments, a sufficient seal for entry into sealed state 4032 is represented by detection before timeout of a vacuum, or negative pressure with respect to atmospheric/ambient pressure, having a predetermined absolute value. In some embodiments the predetermined value may be between −0.5" Hg and −3" Hg, for example between about −1 and −2" Hg, more particularly between about −1.25" and −1.75", for example about −1.5" Hg. A measured negative pressure value of −1.5" Hg was chosen in some embodiments to be −0.5" Hg below a baseline value of about −1" Hg, below which pressure measurements may not yield useful or reliable information. Such a non-zero baseline value may be due at least in part to backpressure or fluid impedance in the pressure measurement path caused by filters or other physical obstructions which may lead measured pressure values to differ from actual pressure values, and particularly to difficulty in measuring negative pressures above −1" Hg due to impedance in the flow path. For systems with a lower baseline pressure measurement values, a lower seal-detection threshold for the measured pressure (e.g. −0.5" Hg) may be used.

Detection of a seal leads to a building-pressure state 4034. Exit from building-pressure state 4034 can occur through timeout, illustrated at 4040, or by achieving a predetermined negative target pressure. In some embodiments, the target pressure has a settable value within an allowed range. In some embodiments, the allowed range may be between about −1" Hg and about −8" Hg, for example between about −3" Hg and about −6" Hg. The lower bound of the range may be set to exclude target pressure values that are considered too low to provide desired user sensations and/or ensure attachment, while the higher bound of the range may be set to a value beyond which device use may be uncomfortable to users. Such an upper bound may depend on device materials and geometry (e.g. suction cavity depth). In manual mode, the target pressure may be changed manually by a user in predetermined increments (e.g. 1" Hg or 0.5" Hg) using plus and minus pressure controls. In autoattach mode the target pressure may be adjusted automatically to maintain attachment as described below. In addition, in an alternating suction mode, the target pressure may be adjusted automatically between user-selected or pre-programmed lower and upper pressure levels.

If the target pressure has been attained before expiration of the timeout interval, the system enters an attachment-confirmation (checking attachment) state 4036. Exit from checking-attachment state 4036 can occur to an attached (maintaining attachment) state 4038 if attachment (pressure at target or within 1" Hg) is confirmed for a predetermined interval (e.g. 1-5 seconds, for example about 2 seconds), or back to building-pressure state 4034 if a leak is detected before expiration of the attachment confirmation time interval. The presence of a leak may be represented by the detection of a negative pressure lower (in absolute value) than the target pressure by a predetermined value (e.g. 1" Hg, larger than an exemplary pump dynamic hysteretic band of 0.5" Hg described below), indicating that the pump suction cannot keep pace with the volume of air leakage. Upon exit back to building-pressure state 4034, in the autoattach mode the target pressure is automatically decremented by a predetermined interval, e.g. about −0.5" Hg or −1" Hg, which represents an increase in the absolute value of the target pressure. Decrementing the target pressure facilitates maintaining attachment under the current, dynamically variable conditions which may depend on the anatomy of the particular user and the way the device is being currently used (e.g. position relative to the user's anatomy, the user's position and range and type of motion, etc.).

In attached (maintaining attachment) state 4038, the pump may be turned on periodically to maintain the measured pressure within a predetermined interval of the target pressure (e.g. ±0.5" Hg), which defines a dynamic hysteretic band of the pump. The pump is turned off otherwise to conserve battery, prevent overheating and maintain user comfort.

An exit to building-pressure state 4034 represents a slow leak. A leak has been detected, but is not necessarily so fast so as to lead to a loss of attachment. Consequently, a decrease in the negative target pressure by a relatively small increment (e.g. −0.5" Hg), representing an increase in the absolute value of the target pressure, may lead to a restoration of attachment in the current dynamic conditions.

An exit from sealed state 4032 to probing-for-seal state 4030 represents a fast leak, one that had led to a measured pressure below −1.5" Hg. In some embodiments, the target pressure is decremented by a larger increment (e.g. about −1" Hg) when such a transition occurs in autoattach mode, to facilitate attachment in more challenging conditions (e.g. the user is moving around more, or has a distinctive anatomy requiring higher suction to maintain attachment).

The exemplary finite state machine states described above effectively track or represent a quality of the seal established between the suction chamber and the user's tissue: different FSM states represent different seal qualities. State transitions triggered by pressure changes while the suction is running effectively track leak events, and are used to automatically increase the target pressure in order to reduce the frequency or probability of device detachment without any immediate user input or interaction. Multiple state transitions, each representing a different leak speed or corresponding seal quality (e.g. corresponding to slow and fast leaks), can be particularly useful because of the inherent time lag between the initiation of pumping and the detection of pressure changes, and because of the transient nature of some leaks. For example, a user may break a seal for just a moment and then readjust position, leading to a transient leak which may be adequately addressed by a small adjustment to the target pressure.

In some embodiments, the target pressure is reset to its default value upon an exit to the pump idle state 4026, or upon detection of any user input (e.g. the press of any button). In some embodiments, an updated default target pressure may be determined and stored in non-volatile memory for future reuse upon determination that a frequency of detachment and/or leak events meets a predetermined condition. For example, if a target pressure of −3" Hg leads to frequent detachment for a particular use, it may be inferred that a lower default target pressure (e.g. −3.5" Hg or −4" Hg, corresponding to a higher absolute value) may be appropriate for that particular user given her anatomy and usage patterns, and that default target pressure is stored in non-volatile memory and reused until a reset event is triggered manually or automatically (e.g. through a long-term timer or determination that detachment events are sufficiently infrequent).

Generally, a lower absolute value of a target pressure needed to maintain an adequate seal is desirable due to patient comfort with lower pressures, and the increased dynamic range available operation in an alternating suction mode. For example, if the target pressure is −3" Hg and the maximum suction pressure in an alternating suction mode is −8" Hg, a dynamic range of 5" Hg is available for the alternating suction mode. A lower dynamic range may lead to decreased sensation as the user's mechanoreceptors adjust over time to a given level of suction.

Figure 11A:
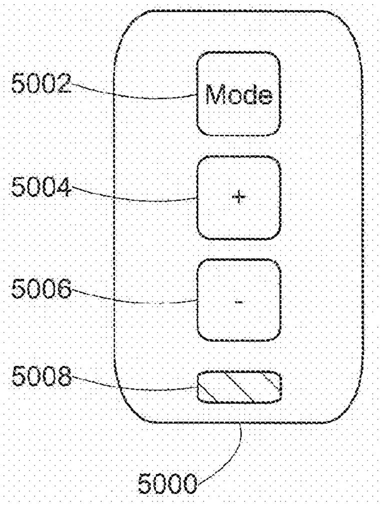
FIG. 11A shows an exemplary on-device user interface according to some embodiments of the present invention.
Figure 11B:
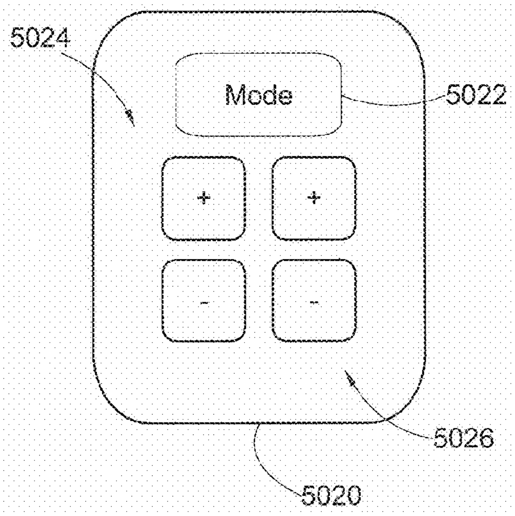
FIG. 11B shows an exemplary dedicated remote control user interface according to some embodiments of the present invention.
Figure 11C:
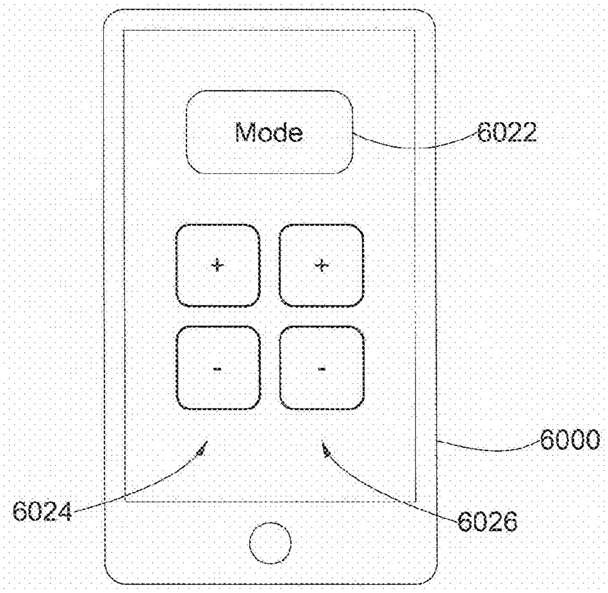
FIG. 11C shows an exemplary smartphone application user interface according to some embodiments of the present invention.

FIGS. 11A-C illustrate exemplary user interfaces suitable for an on-device interface (FIG. 11A), a remote control (FIG. 11B), and a remote control implemented as an application running on a smartphone or other general-purpose mobile device (FIG. 11C), according to some embodiments of the present invention. The exemplary illustrated user interface designs embody a given tradeoff between ease/simplicity of use on the one hand, and customizability of operation on the other.

An on-device user interface 5000 includes a mode button 5002, plus and minus buttons 5004, 5006, and a display LED 5008. The display LED 5008 may be positioned to face downward as the device is used. A user interface 5020 implemented on a remote control may have a larger surface available for controls, and may include a mode button 5022, and two separate plus-minus button pairs 5024, 5026, each controlling a different parameter or device (e.g. suction and stimulators). A similar design may be used in a smartphone user interface 6000, which includes a mode button 6022 and two level-adjustment button pairs 6024, 6026.

In some embodiments, the mode button controls device transitions between manual and automatic (autoattach) operation modes. In some embodiments, at least some interactions with the mode button (e.g. a short/long press on the on-device mode button) may control transitions between suction/pressure control and stimulator control operation modes for the level adjustment (plus minus) buttons. Exemplary embodiments are described below.

In some embodiments, the on-device user interface level-adjustment buttons 5004, 5006 default to a mechanical stimulator control mode, and the device is by default in an automatic attachment operation mode. A short press on the mode button 5002 changes the response to level-adjustment buttons 5004, 5006 to a suction/pressure control mode for a predetermined time period (e.g. 5 or 10 seconds), after which the system reverts to its default.

In some embodiments, all mechanical stimulators are turned off automatically upon a transition to suction control mode. Turning off the mechanical stimulators signals to the user that the device is now in suction control mode, and allows the user to more finely choose a desired level of suction without sensory (tactile and auditory) interference from the motors. Once attachment is established, the level control buttons revert to mechanical stimulator control mode and the mechanical stimulators can start (or restart).

In some embodiments, a long press on one of the mode buttons triggers entry into an alternating suction mode. In some embodiments, the default peak suction pressure upon entry into the alternating suction mode is at target, so the user has to press a plus button at least once to initiate alternating suction; subsequent presses of the plus/minus buttons increment/decrement the peak suction level. In some embodiments, the default peak suction pressure can also be set to be at one plus target when the alternating suction mode is started.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An apparatus for intensifying sexual arousal in a female user, comprising:

- at least one stimulator;
- a tissue-contacting chamber including a suction chamber;
- a suction pump in fluid communication with the tissue-contacting chamber;
- a pressure sensor in fluid communication with the tissue contacting chamber; and
- a pump controller electrically connected to the suction pump and the pressure sensor, the pump controller comprising at least one processor configured to:
  - identify an attachment of the tissue-contacting chamber to user tissue in response to a positive pressure indicator received from the pressure sensor, the positive pressure indicator indicating a pressure level above ambient pressure; and
  - in response to identifying the attachment, automatically start the suction pump to secure the tissue-contacting chamber to the user tissue by reducing a pressure within the tissue-contacting chamber to below ambient pressure.

2. The apparatus of claim 1, wherein the pump controller is configured to receive a signal indicative of a user input selecting one of a manual and an automatic attachment operating mode for the apparatus, wherein the pump controller is configured to automatically start the suction pump in response to identifying the attachment only in the automatic attachment mode and not in the manual operating mode.

3. The apparatus of claim 1, wherein the pump controller is further configured to automatically stop the suction pump in response to an indicator from the pressure sensor.

4. The apparatus of claim 3, wherein the indicator comprises a measured negative pressure value having an absolute value below an absolute value of a predetermined target pressure for the tissue-contacting chamber.

5. The apparatus of claim 4, wherein the indicator comprises a measured negative pressure value having an absolute value below a predetermined fixed threshold, the fixed threshold being between about 0.5" Hg and about 2" Hg.

6. The apparatus of claim 1, wherein the pump controller is further configured to operate in an attachment-maintenance mode by automatically starting and stopping the suction pump in response to measured pressure values received from the pressure sensor differing by a predetermined amount from a target pressure.

7. The apparatus of claim 1, wherein the pump controller is further configured to automatically adjust a target negative pressure for the tissue-contacting chamber in response to receiving a leak indicator from the pressure sensor.

8. The apparatus of claim 7, wherein the leak indicator comprises a measured negative pressure value having an absolute value below an absolute value of the negative target pressure for the tissue-contacting chamber.

9. The apparatus of claim 1, wherein the at least one stimulator is flexibly suspended at least partially within the suction chamber.

10. A system for controlling a suction pump, comprising:
at least one hardware processor;
a non-transitory computer-readable medium storing instructions which, when executed by at least one hardware processor, cause the at least one processor to:
in response to a positive pressure indicator received from a pressure sensor, identify an attachment to user tissue of a tissue-contacting chamber of an apparatus for intensifying sexual arousal in a female user, the positive pressure indicator indicating a pressure level above ambient pressure; and
in response to identifying the attachment, automatically start a suction pump of the apparatus to secure the tissue-contacting chamber to the user tissue by reducing a pressure within the tissue-contacting chamber to below ambient pressure.

11. A system for controlling a suction pump, comprising:
at least one hardware processor;
a non-transitory computer-readable medium storing instructions which, when executed by at least one hardware processor, cause the at least one processor to:
receive user input identifying a manual operating mode for an apparatus for intensifying sexual arousal in a female user, the apparatus comprising a suction pump and a pressure sensor in fluid communication with a tissue-contacting chamber;
receive user input identifying an autoattach operating mode for the apparatus, wherein in the autoattach mode, the apparatus is configured to:
identify an attachment of the tissue-contacting chamber to user tissue in response to a positive pressure indicator received from the pressure sensor, the positive pressure indicator indicating a pressure level above ambient pressure; and
in response to identifying the attachment, automatically start the suction pump to secure the tissue-contacting chamber to the user tissue by reducing a pressure within the tissue-contacting chamber to below ambient pressure.

12. An apparatus for controlling a suction pump, comprising:
a tissue-contacting chamber;
a suction pump in fluid communication with the tissue-contacting chamber;
a pressure sensor in fluid communication with the tissue contacting chamber; and
a pump controller electrically connected to the suction pump and the pressure sensor, the pump controller comprising at least one processor configured to:
determine, according to at least one pressure value received from the pressure sensor, a seal quality indicator representing a quality of a seal formed between a boundary of the tissue-contacting chamber and user tissue;
determine a target negative pressure for the tissue-contacting chamber according to the seal quality indicator; and
control the suction pump according to the target negative pressure.

13. The apparatus of claim 12, wherein the pump controller is further configured to automatically stop the suction pump in response to receiving a leak indicator from the pressure sensor.

14. The apparatus of claim 13, wherein the at least one pressure value is a negative pressure value having an absolute value below an absolute value of a predetermined target pressure for the tissue-contacting chamber.

15. A system for controlling a suction pump, comprising:
at least one hardware processor;
a non-transitory computer-readable medium storing instructions which, when executed by at least one hardware processor, cause the at least one processor to:
determine, according to at least one pressure value received from a pressure sensor of an apparatus for intensifying sexual arousal in a female user, a seal quality indicator representing a quality of a seal formed between a boundary of a tissue-contacting chamber of the apparatus and user tissue;
determine a target negative pressure for the tissue-contacting chamber according to the seal quality indicator; and
control a suction pump of the apparatus according to the target negative pressure.

* * * * *